United States Patent
Chou et al.

(10) Patent No.: US 10,656,149 B2
(45) Date of Patent: May 19, 2020

(54) ANALYTE DETECTION ENHANCEMENT BY TARGETED IMMOBILIZATION, SURFACE AMPLIFICATION, AND PIXELATED READING AND ANALYSIS

(71) Applicant: THE TRUSTEES OF PRINCETON UNIVERSITY, Princeton, NJ (US)

(72) Inventors: Stephen Y. Chou, Princeton, NJ (US); Liang-Cheng Zhou, Princeton, NJ (US)

(73) Assignee: THE TRUSTEES OF PRINCETON UNIVERSITY, PRINCETON, NJ (US)

( * ) Notice: Subject to any disclaimer, the term of this patent is extended or adjusted under 35 U.S.C. 154(b) by 891 days.

(21) Appl. No.: 14/775,638

(22) PCT Filed: Mar. 14, 2014

(86) PCT No.: PCT/US2014/028417
§ 371 (c)(1),
(2) Date: Sep. 11, 2015

(87) PCT Pub. No.: WO2014/144133
PCT Pub. Date: Sep. 18, 2014

(65) Prior Publication Data
US 2016/0033496 A1    Feb. 4, 2016

Related U.S. Application Data

(60) Provisional application No. 61/801,096, filed on Mar. 15, 2013.

(51) Int. Cl.
G01N 33/543    (2006.01)
G01N 33/574    (2006.01)
G02B 21/00    (2006.01)

(52) U.S. Cl.
CPC . G01N 33/54386 (2013.01); G01N 33/57473 (2013.01); G02B 21/008 (2013.01)

(58) Field of Classification Search
None
See application file for complete search history.

(56) References Cited

U.S. PATENT DOCUMENTS

| 5,329,461 A * | 7/1994 | Allen | G01N 15/1475 |
| | | | 324/71.4 |
| 2005/0176029 A1* | 8/2005 | Heller | B82Y 5/00 |
| | | | 435/6.11 |
| 2006/0147927 A1* | 7/2006 | Geddes | C12Q 1/6816 |
| | | | 435/6.12 |
| 2009/0303472 A1 | 12/2009 | Zhao et al. | |
| 2011/0005932 A1 | 1/2011 | Jovanovich et al. | |

FOREIGN PATENT DOCUMENTS

| WO | WO2012024006 | 2/2012 | |
| WO | WO-2012024006 A2 * | 2/2012 | ......... G01N 21/6452 |
| WO | WO2013154770 | 10/2013 | |

OTHER PUBLICATIONS

Choe et al., Fc-Binding Ligands of Immunoglobulin G: An Overview of High Affinity Proteins and Peptides, Materials 2016, 9, 994, 1-17 (Year: 2016).*
Li et al. "Three-dimensional cavity nanoantenna coupled plasmonic nanodots for ultrahigh and uniform surface-enhanced Raman scattering over large area", Optics Express, 2011, 19(5): 3925-3936.
Zhou et al., "Enhancement of Immunoassay's Fluorescence and Detection Sensitivity Using Three-Dimensional Plasmonic Nano-Antenna-Dots Array", Analytical Chemistry, 2012, 84: 4489-4495.

* cited by examiner

Primary Examiner — Andrea S Grossman
(74) Attorney, Agent, or Firm — James S. Keddie; Bozicevic, Field & Francis LLP

(57) ABSTRACT

This disclosure provides, among other things, a method of sample analysis, that comprises: (a) binding target analytes to capture agents that are attached to a surface of a plate, wherein the plate comprises (i) a sensing amplification layer comprises nanostructures that enhance signals and (ii) the capture agents are attached to said sensing amplification layer; (b) reading the plate with a reading device to produce an image of signals that represent individual binding events; and (c) identifying and counting individual binding events in an area of the image, thereby providing an estimate of the amount of one or more analytes in the sample. A system for performing the method is also provided.

25 Claims, 15 Drawing Sheets

ANALYTE DETECTION ENHANCEMENT BY TARGETED IMMOBILIZATION, SURFACE AMPLIFICATION, AND PIXELATED READING AND ANALYSIS

CROSS-REFERENCING

This application is a 371 National Phase of PCT/US2014/028417, filed Mar. 14, 2014, which claims the benefit of U.S. Provisional Patent Application Ser. No. 61/801,096, filed on Mar. 15, 2013 (NSNR-005PRV) which applications are incorporated by reference herein for all purposes.

STATEMENT REGARDING FEDERALLY SPONSORED RESEARCH

This invention was made with government support under Grant No. FA9550-08-1-0222 awarded by the United States Air Force, Office of Scientific Research. The government has certain rights in this invention.

BACKGROUND

The invention is related to the methods and systems that can improve the sensing of an analyte. The analyte include proteins, peptides, DNA, RNA, nucleic acid, small molecules, cells, nanoparticles with different shapes. The targeted analyte can be either in a solution or in air or gas phase. The sensing includes the detection of the existence, quantification of the concentration, and determination of the states of the targeted analyte.

SUMMARY

The following brief summary is not intended to include all features and aspects of the present invention, nor does it imply that the invention must include all features and aspects discussed in this summary.

This disclosure provides, among other things, methods and systems that can improve the sensing of an analyte. The analyte include proteins, peptides, DNA, RNA, nucleic acid, small molecules, cells, nanoparticles with different shapes. The targeted analyte can be either in a solution or in air or gas phase. The sensing includes the detection of the existence, quantification of the concentration, and determination of the states of the targeted analyte. The methods use (a) a solid substrate with one surface covered by a layer of material, termed "the sensing amplification layer" or SAL, that can significantly amplify the to-be-sensed signal generated only within a small distance from the surface of the SAL (which is called detection zone); (b) immobilization of targeted analytes, and (c) pixelated reading and analysis of the electromagnetic signal. The SAL amplifies the electromagnetic signal (e.g. electrical, optical) generated by the molecules immobilized on the SAL surface without amplify or without amplify significantly the number of the molecules. Such amplification plus the very small depth (~100 nm) of the amplification zone lead to the advantages (i) high sensitivity (i.e. better limit of detection), (ii) order of magnitude shorter in total reading time, (iii) use of less sensitive or expensive reader for a given detection performance, and (iv) linear amplification and higher dynamic range. Furthermore, electric field is also used to assist molecular selectivity, or bonding, and detection.

BRIEF DESCRIPTION OF THE DRAWINGS

The skilled artisan will understand that the drawings, described below, are for illustration purposes only. The drawings are not intended to limit the scope of the present teachings in any way. Some of the drawings are not in scale.

Corresponding reference numerals indicate corresponding parts throughout the several figures of the drawings. It is to be understood that the drawings are for illustrating the concepts set forth in the present disclosure and are not to scale.

Figure 1:
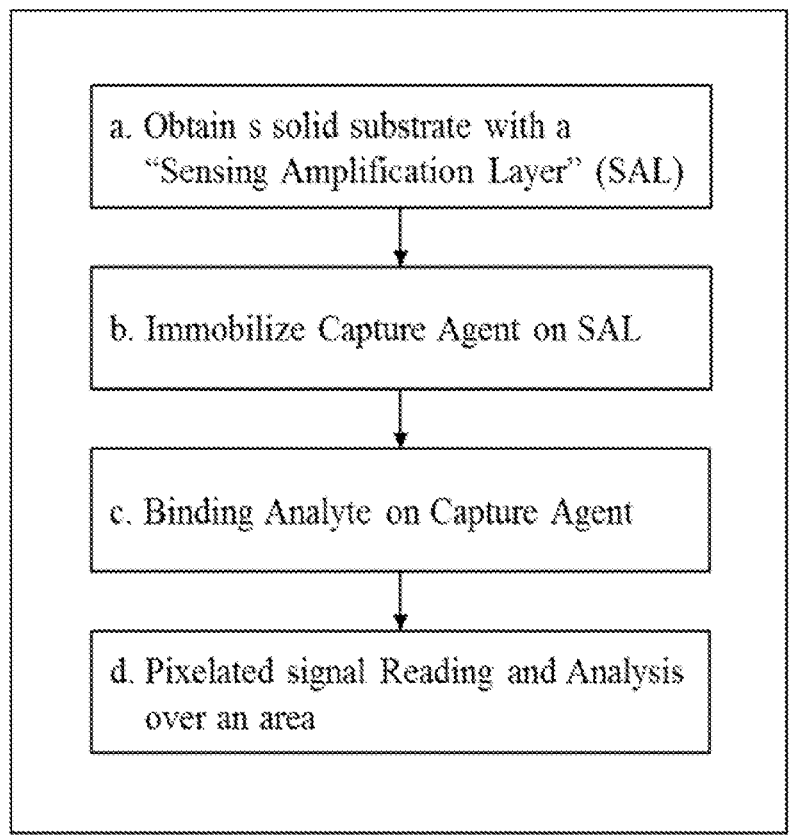
FIG. 1 is a flow chart of method for analyte detection enhancement using surface-zone-amplification, and pixelated reading and analysis.

Before any embodiments of the invention are explained in detail, it is to be understood that the invention is not limited in its application to the details of construction and the arrangement of components set forth in the following description or illustrated in the drawings.

DEFINITIONS

Before describing exemplary embodiments in greater detail, the following definitions are set forth to illustrate and define the meaning and scope of the terms used in the description.

Figure 12:
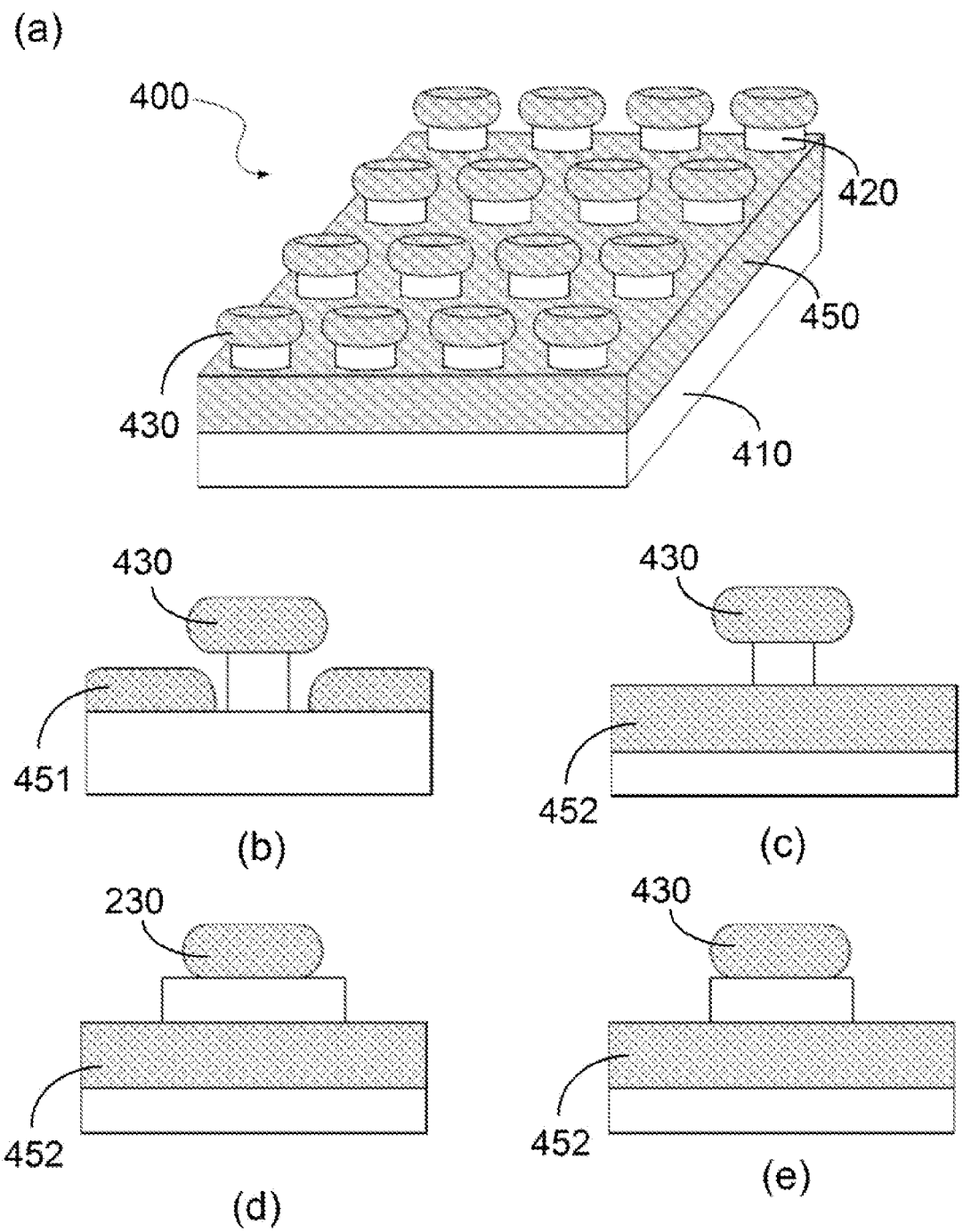
FIG. 12. Schematic of Disk-on-Pillar (DoP) structure (400). (a) overview of general structure. (b) Cross-section of one embodiment where the back metallic film is around and next to the pillars which are dielectric or semiconductor. (c, d, e) cross-section of another embodiment, where the metallic film is a sheet of film go under the disk, but the pillars have different lateral dimension than that of the disks.
Figure 13:
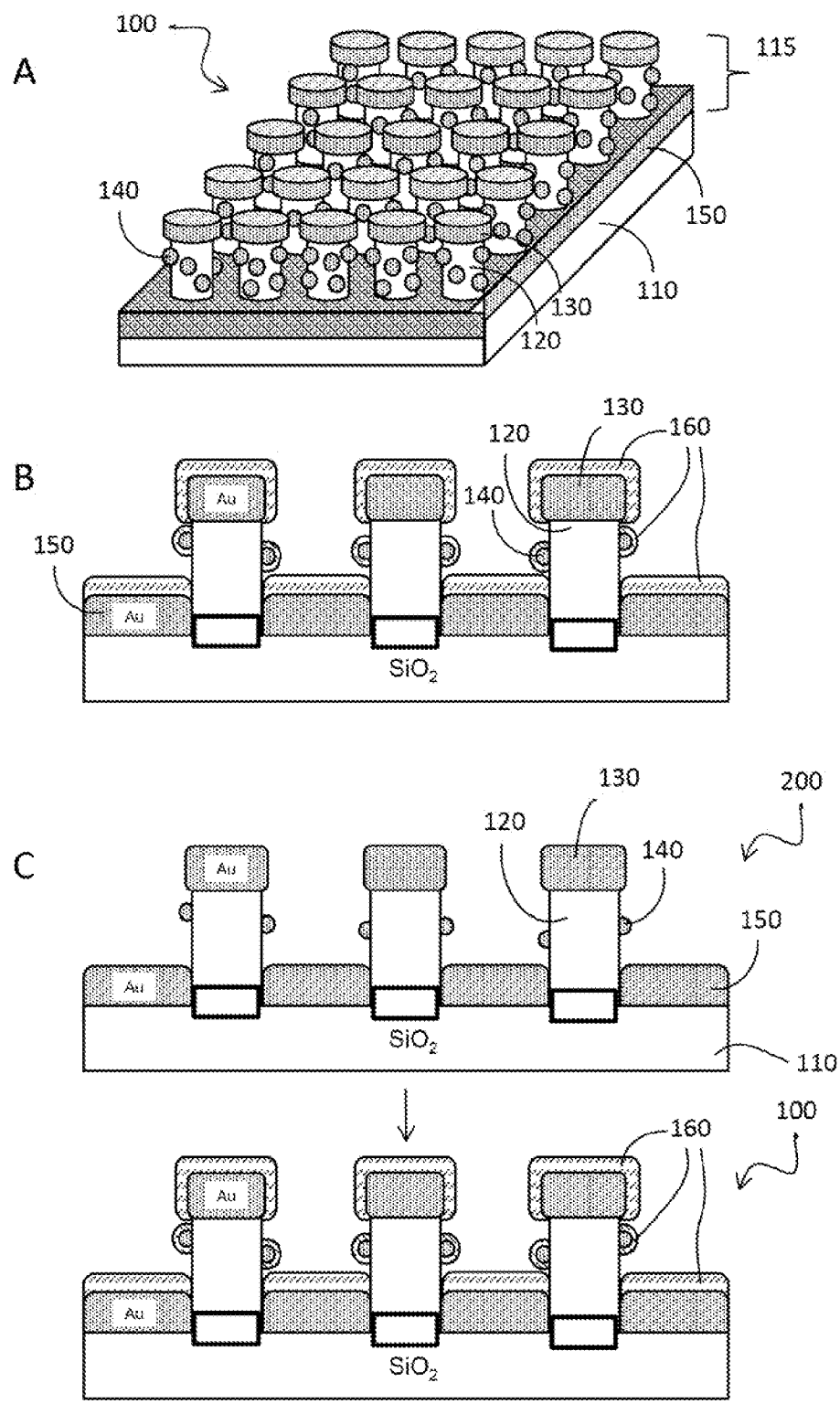
FIG. 13. Schematic of disk-coupled dots-on-pillar antenna array (D2PA) plate with a molecular linking layer. (A) Overview of D2PA plate without an immunoassay. (b) Cross-section after coating the molecular linking layer (also termed "molecular adhesion layer") (160). (c) Before and after coating the molecular linking layer.

The terms "disk-coupled dots-on-pillar antenna array" and "D2PA" as used herein refer to the device illustrated in in FIGS. 12 and 13, where the array 100 comprises: (a) substrate 110; and (b) a D2PA structure, on the surface of the substrate, comprising one or a plurality of pillars 115 extending from a surface of the substrate, wherein at least one of the pillars comprises a pillar body 120, metallic disc 130 on top of the pillar, metallic back plane 150 at the foot of the pillar, the metallic back plane covering a substantial portion of the substrate surface near the foot of the pillar; metallic dot structure 130 disposed on sidewall of the pillar. The D2PA amplifies a light signal that is proximal to the surface of the D2PA. The D2PA enhances local electric field and local electric field gradient in regions that is proximal to the surface of the D2PA. The light signal includes light scattering, light diffraction, light absorption, nonlinear light generation and absorption, Raman scattering, chromaticity, luminescence that includes fluorescence, electroluminescence, chemiluminescence, and electrochemiluminescence.

A D2PA array may also comprise a molecular adhesion layer that covers at least a part of said metallic dot structure, said metal disc, and/or said metallic back plane and, optionally, a capture agent that specifically binds to an analyte, wherein said capture agent is linked to the molecular adhesion layer of the D2PA array. The nanosensor can amplify a light signal from an analyte, when said analyte is bound to the capture agent. One preferred SAL embodiment is that the dimension of one, several or all critical metallic and dielectric components of SAL are less than the wavelength of the light in sensing. Details of the physical structure of disk-coupled dots-on-pillar antenna arrays, methods for their fabrication, methods for linking capture agents to disk-coupled dots-on-pillar antenna arrays and methods of using disk-coupled dots-on-pillar antenna arrays to detect analytes are described in a variety of publications including WO2012024006, WO2013154770, Li et al (Optics Express 2011 19, 3925-3936), Zhang et al (Nanotechnology 2012 23: 225-301); and Zhou et al (Anal. Chem. 2012 84: 4489) which are incorporated by reference for those disclosures.

The term "molecular adhesion layer" refers to a layer or multilayer of molecules of defined thickness that comprises an inner surface that is attached to the D2PA nanodevice and an outer (exterior) surface can be bound to capture agents.

The term "capture agent-reactive group" refers to a moiety of chemical function in a molecule that is reactive with capture agents, i.e., can react with a moiety (e.g., a hydroxyl, sulfhydryl, carboxy or amine group) in a capture agent to produce a stable strong, e.g., covalent bond.

The term "capture agent" as used herein refers to an agent that binds to a target analyte through an interaction that is sufficient to permit the agent to bind and concentrate the target molecule from a heterogeneous mixture of different molecules. The binding interaction is typically mediated by an affinity region of the capture agent. Typical capture agents include any moiety that can specifically bind to a target analyte. Certain capture agents specifically bind a target molecule with a dissociation constant ($K_D$) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to as low as $10^{-16}$ M) without significantly binding to other molecules. Exemplary capture agents include proteins (e.g., antibodies), and nucleic acids (e.g., oligonucleotides, DNA, RNA including aptamers).

The terms "specific binding" and "selective binding" refer to the ability of a capture agent to preferentially bind to a particular target molecule that is present in a heterogeneous mixture of different target molecule. A specific or selective binding interaction will discriminate between desirable (e.g., active) and undesirable (e.g., inactive) target molecules in a sample, typically more than about 10 to 100-fold or more (e.g., more than about 1000- or 10,000-fold).

The term "protein" refers to a polymeric form of amino acids of any length, i.e. greater than 2 amino acids, greater than about 5 amino acids, greater than about 10 amino acids, greater than about 20 amino acids, greater than about 50 amino acids, greater than about 100 amino acids, greater than about 200 amino acids, greater than about 500 amino acids, greater than about 1000 amino acids, greater than about 2000 amino acids, usually not greater than about 10,000 amino acids, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Also included by these terms are polypeptides that are post-translationally modified in a cell, e.g., glycosylated, cleaved, secreted, prenylated, carboxylated, phosphorylated, etc., and polypeptides with secondary or tertiary structure, and polypeptides that are strongly bound, e.g., covalently or non-covalently, to other moieties, e.g., other polypeptides, atoms, cofactors, etc.

The term "antibody" is intended to refer to an immunoglobulin or any fragment thereof, including single chain antibodies that are capable of antigen binding and phage display antibodies).

The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The term "complementary" as used herein refers to a nucleotide sequence that base-pairs by hydrogen bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. Typically, "complementary" refers to a nucleotide sequence that is fully complementary to a target of interest such that every nucleotide in the sequence is complementary to every nucleotide in the target nucleic acid in the corresponding positions. When a nucleotide sequence is not fully complementary (100% complementary) to a non-target sequence but still may base pair to the non-target sequence due to complementarity of certain stretches of nucleotide sequence to the non-target sequence, percent complementarily may be calculated to assess the possibility of a non-specific (off-target) binding. In general, a complementary of 50% or less does not lead to non-specific binding. In addition, a complementary of 70% or less may not lead to non-specific binding under stringent hybridization conditions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 200 nucleotides and up to 300 nucleotides in length, or longer, e.g., up to 500 nt in length or longer. Oligonucleotides may be synthetic and, in certain embodiments, are less than 300 nucleotides in length.

The term "attaching" as used herein refers to the strong, e.g, covalent or non-covalent, bond joining of one molecule to another.

The term "surface attached" as used herein refers to a molecule that is strongly attached to a surface.

The term "sample" as used herein relates to a material or mixture of materials containing one or more analytes of interest. In particular embodiments, the sample may be obtained from a biological sample such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In particular embodiments, a sample may be obtained from a subject, e.g., a human, and it may be processed prior to use in the subject assay. For example, prior to analysis, the protein/nucleic acid may be extracted from a tissue sample prior to use, methods for which are known. In particular embodiments, the sample may be a clinical sample, e.g., a sample collected from a patient.

The term "analyte" refers to a molecule (e.g., a protein, nucleic acid, or other molecule) that can be bound by a capture agent and detected.

The term "assaying" refers to testing a sample to detect the presence and/or abundance of an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminscence. An external excitation can be a combination of the above.

The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The term "hybridization" refers to the specific binding of a nucleic acid to a complementary nucleic acid via Watson-Crick base pairing. Accordingly, the term "in situ hybridization" refers to specific binding of a nucleic acid to a metaphase or interphase chromosome.

The terms "hybridizing" and "binding", with respect to nucleic acids, are used interchangeably.

The term "capture agent/analyte complex" is a complex that results from the specific binding of a capture agent with an analyte. A capture agent and an analyte for the capture agent will usually specifically bind to each other under "specific binding conditions" or "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens and nucleic acid hybridization are well known in the art (see, e.g., Harlow and Lane (Antibodies: A Laboratory Manual Cold Spring Harbor Laboratory, Cold Spring Harbor, N.Y. (1989) and Ausubel, et al, Short Protocols in Molecular Biology, 5th ed., Wiley & Sons, 2002).

The term "specific binding conditions" as used herein refers to conditions that produce nucleic acid duplexes or protein/protein (e.g., antibody/antigen) complexes that contain pairs of molecules that specifically bind to one another, while, at the same time, disfavor to the formation of complexes between molecules that do not specifically bind to one another. Specific binding conditions are the summation or combination (totality) of both hybridization and wash conditions, and may include a wash and blocking steps, if necessary.

For nucleic acid hybridization, specific binding conditions can be achieved by incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

For binding of an antibody to an antigen, specific binding conditions can be achieved by blocking a substrate containing antibodies in blocking solution (e.g., PBS with 3% BSA or non-fat milk), followed by incubation with a sample containing analytes in diluted blocking buffer. After this incubation, the substrate is washed in washing solution (e.g. PBS+TWEEN 20) and incubated with a secondary capture antibody (detection antibody, which recognizes a second site in the antigen). The secondary capture antibody may conjugated with an optical detectable label, e.g., a fluorophore such as IRDye800CW, Alexa 790, Dylight 800. After another wash, the presence of the bound secondary capture antibody may be detected. One of skill in the art would be knowledgeable as to the parameters that can be modified to increase the signal detected and to reduce the background noise.

The term "a secondary capture agent" which can also be referred to as a "detection agent" refers a group of biomolecules or chemical compounds that have highly specific affinity to the antigen. The secondary capture agent can be strongly linked to an optical detectable label, e.g., enzyme, fluorescence label, or can itself be detected by another detection agent that is linked to an optical detectable label through bioconjugatio (Hermanson, "Bioconjugate Techniques" Academic Press, 2nd Ed., 2008).

The term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least 10-8M. A biotin affinity agent may also include a linker, e.g., -LC-biotin, -LC-LC-Biotin, -SLC-Biotin or -PEGn-Biotin where n is 3-12.

The term "streptavidin" refers to both streptavidin and avidin, as well as any variants thereof that bind to biotin with high affinity.

The term "marker" refers to an analyte whose presence or abundance in a biological sample is correlated with a disease or condition.

The term "bond" includes covalent and non-covalent bonds, including hydrogen bonds, ionic bonds and bonds produced by van der Waal forces.

The term "amplify" refers to an increase in the magnitude of a signal, e.g., at least a 10-fold increase, at least a 100-fold increase at least a 1,000-fold increase, at least a 10,000-fold increase, or at least a 100,000-fold increase in a signal.

The term "local" refers to "at a location",

Other specific binding conditions are known in the art and may also be employed herein.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, and reference to "a detection agent" includes a single detection agent and multiple detection agents.

DETAILED DESCRIPTION OF EXEMPLARY EMBODIMENTS

The following detailed description illustrates some embodiments of the invention by way of example and not by way of limitation.

The invention is related to the methods and systems that can improve the sensing of an analyte. The analyte include proteins, peptides, DNA, RNA, nucleic acid, small molecules, cells, nanoparticles with different shapes. The targeted analyte can be either in a solution or in air or gas phase.

The sensing includes the detection of the existence, quantification of the concentration, and determination of the states of the targeted analyte.

Figure 2:
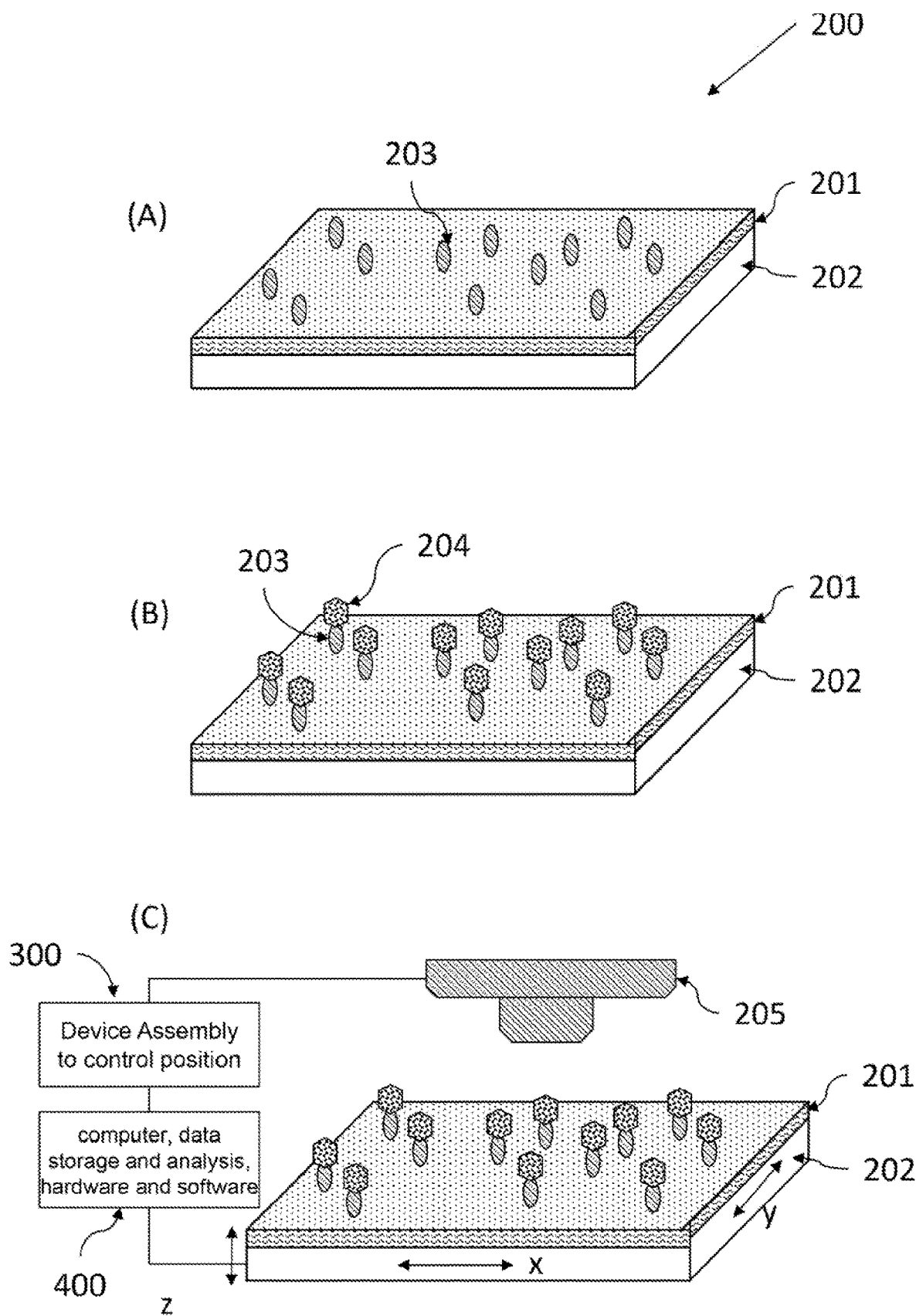
FIG. 2 is the schematics of a method of analyte detection enhancement by targeted immobilization, surface amplification, and pixelated reading and analysis. (A) Capture agents immobilized on the surface of a substrate with one surface covered by a layer of material, termed "the sensing amplification layer" or SAL. (B) specific binding of analytes to the capture agents on the SAL surface. (C) Reading the plate with a reading device to produce an image of signals that represent individual binding events. A device assembly, that holds the plate and the imager, controls or changes the relative position between the plate and the reading device, in at least one of the three (x, y, z) orthogonal directions, for reading the signal. An electronics and a data storage for storing said image, and a computer comprising programming for identifying and counting individual binding events in an area of the image, thereby providing an estimate of the amount of one or more analytes in the sample.

As shown in FIG. 1 and FIG. 2, in one embodiment of the invention, a method of improving a sensing of an analyte in a solution or a gas phase comprises:

(a) obtaining the plate 200 that comprises a substrate 202 with one surface covered by a layer of material, termed "the sensing amplification layer" or SAL 201 comprises nanostructures that amplifies the to-be-sensed signal generated only within a small distance from the surface of the SAL (which is called detection zone);

(b) immobilizing capture agents 203 on the SAL 201 surface;

(c) binding analytes 204 to the capture agents on the SAL 201 surface;

(d) reading the plate with a reading device 205 in a pixelated manner to produce an image of signals that represent individual binding events; and (e) analyzing the 2D signal map to identify and count individual binding events in an area of the image, thereby providing an estimate of the amount of one or more analytes in the sample.

Before the step (c), the above method can further include a step of labeling the target analytes with a label 209, either prior to or after they are bound to said capture agents.

Compared with lumped signal reading, where the signal from the entire detection areas are measured together, the pixelated reading pick signal on each pixel and remove a strong background in the detection area, leading to higher sensitivity (i.e. better limit of detection) and wider dynamic range. The use of the SAL significantly enhances the advantages of the pixelated reading to achieve even higher sensitivity and wider dynamics range.

Figure 3:
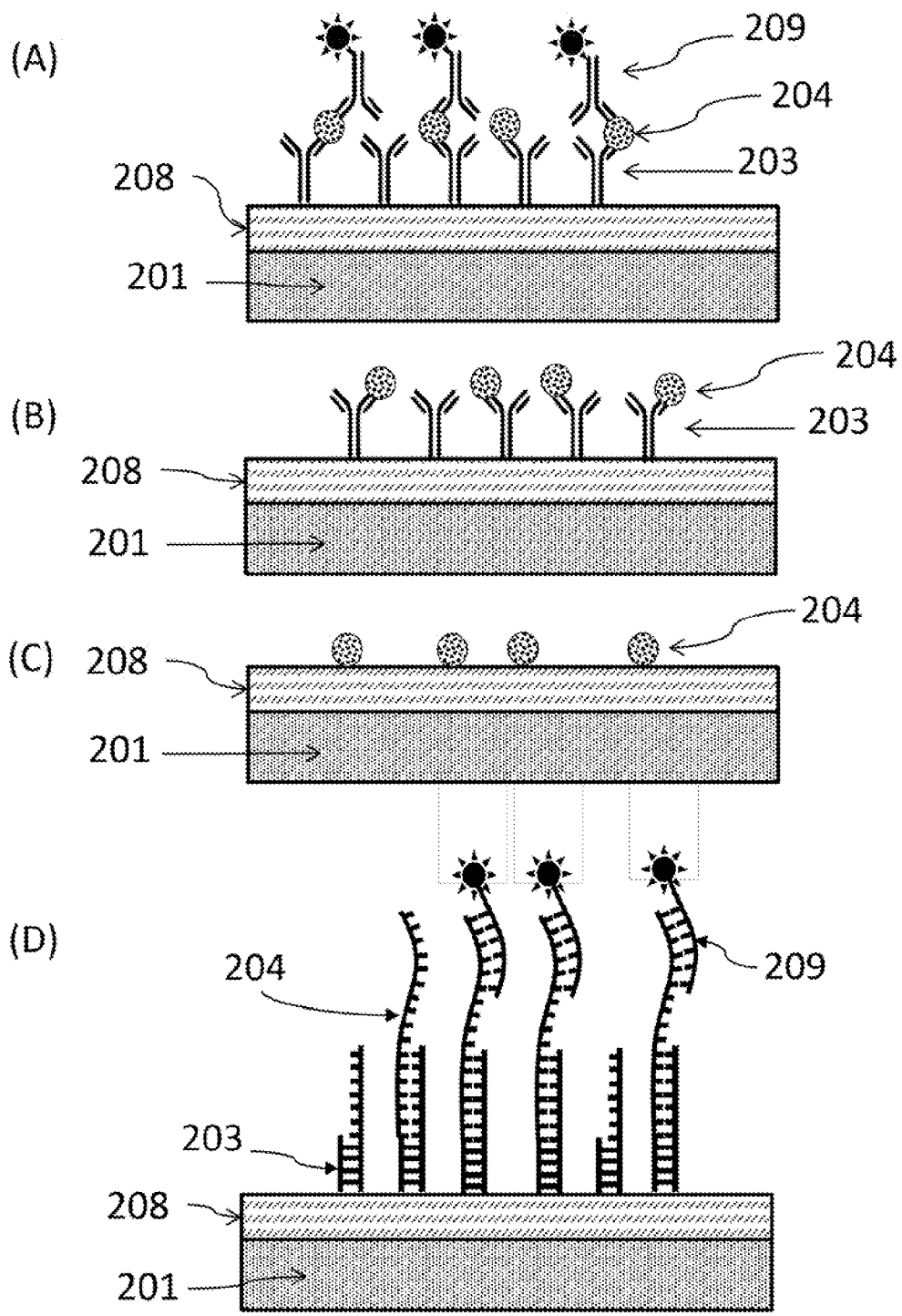
FIG. 3 schematically illustrates exemplary analytes, assay plate structures with the "sensing amplification layer" SAL. (A) Analytes are protein with detection labels. (B) Analytes are proteins without using additional detection label. (C) Analytes are small molecules. And (D) analytes are DNA or RNA. MSA is optional. Capture agents may directly attach to the SAL. (Drawing not to scale)

FIG. 3 schematically illustrates exemplary analytes, assay plate structures with the "sensing amplification layer" SAL 201 and optional molecular spacer/adhesion layer (MSA) 208. (A) Analytes are protein with detection labels 209. (B) Analytes are proteins without using additional detection label. (C) Analytes are small molecules. And (D) analytes are DNA or RNA. MSA 208 is optional. Capture agents may directly attach to the SAL.

Applying External Electric Field

In other embodiments, a voltage bias, which generates an electric field and electric field gradient, is applied to either during the selective binding of the analytes or during the signal measurements, to improve (1) the selectivity and the binding quality, (2) the binding speed, and (3) detection signal and hence detection sensitivity (i.e. better limit of detection) and or detection speed. One of the reasons is that the electric field and/or the electric field gradient can accelerate the movement of analytes that have been placed in solution on the surface of the plate to the capture agents on the sensing amplification layer, and can align the analytes and/or capture agents to a better position for bonding and/or sensing.

Figure 4:
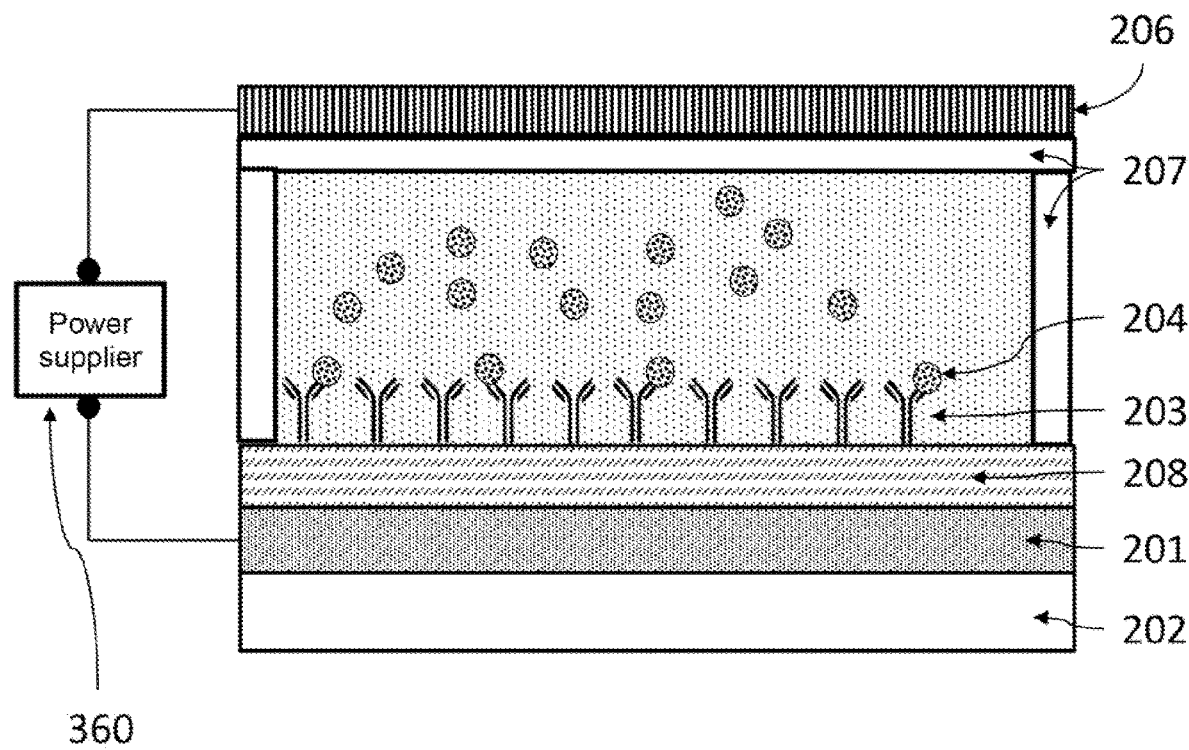
FIG. 4 schematically illustrates an embodiment of an E-field assisted immunoassay. The voltage supplied between the "sensing amplification layer" (SAL) and a counter electrode. The SAL enhances local E-field and E-field gradient, which in turn enhance the assaying properties, including improve the sensing sensitivity and reducing incubation time.

In one of the embodiments, the SAL 201 can serves as one electrode and a conducting plate 206 will be used as the second electrode. A voltage bias (i.e. voltage difference) can be applied using a power supply, 360. The voltage bias creates electric field and electric field gradient. A DC-field will be applied. Two electrodes are separated in the order of mm and the Voltage applied between the electrodes is 0.1V to 1000V (see FIG. 4), depending upon the spacing 207 between the electrodes. In some cases, an AC field can be used, the peak-to-peak voltage applied between the electrodes is 0.1 V to 1000 V and the frequency is from 100 Hz to 1000 MHz. For using DEP force, both DC and AC works, so we can claim AC. The exact voltage bias to be used depends on the required electric field and/or the electric field gradient.

Targeted Analyte Surface Concentration

The method can be used for measuring the concentration of the analytes where the immobilized analytes are significantly spatial separated, or are overlap each other on a solid surface substrate.

Substrates

The substrate 202 above can be any forms as long as it has solid phase on its surface, and hence including a rigid or flexible solid plate or thin film of any materials, as long as the materials and their forms do not significantly interfere with the sensing.

Surface Amplification

The amplification above means to amplify the electromagnetic signal (e.g. electrical, optical, and their combination and in different wavelengths) generated by the molecules 203, 204 immobilized on the SAL surface 201 without amplify or without amplify significantly the number of the molecules.

The significant amplification above means the amplification is at least 100 times higher than that on the surface of a glass, a plastic, or a flat metallic film.

The small distance from the surface of the SAL 201 within which that the to-be-sensed signal are amplified, namely the depth of the detection zone is about 150 nm or less, and typically 80 nm or less for luminescence and 60 nm or less for Raman scattering.

Advantages of Surface Amplification Layer (SAL)

The key advantages of using the SAL are several.

(1) Since the SAL amplifies only the signal that are generated within a small distance from its surface where the analytes are immobilized (i.e. within the depth of the detection zone), the interference signals generated by the molecules outside the detection zone will interfere less with the signals generated within the detection zone; higher the amplification and less the interference. Hence, the SAL will increase the detection sensitivity of targeted analytes, and the higher the amplificaiton and the higher the increase.

(2) The SAL zone-amplification also reduces the signal reading time for a given sensing sensitivity or detection limit. This has a significant practical implication to the use of pixelated reading, since such reading often involves a large number of pixels of 1,000 to 10,000,000, and any time saving on one pixel will lead to the time saving of 1,000 to 10,000,000 fold. Hence the SAL zone amplification will make the pixelated reading, that are previously impossible, possible.

(3) The SAL zone-amplification also allows to the use of lower sensitive detectors and hence enables the use of the reading systems that are portable and/or low cost, which will in turn significantly increases the broad usages of the invented method.

(4) The SAL zone-amplification amplifies the signal more or less proportional to the targeted analytes (i.e. linear with the analytes), rather nonlinear in the most sensing methods that are based on the amplification of the number of molecules. It leads to better sensitivities and wider dynamic range.

The current inventions with the SAL differ from the prior arts in many ways including the following. (a) The prior arts do not have the SAL. (b) The prior arts use ELISA or other methods that needs to an amplification of the number of the molecules to achieve a detectable signal. But the current invention does not. (c) Some of the prior arts attach nanoparticles, after having immobilized the targeted analytes on the surfaced, to amplify the signal. These nanoparticles are sitting on top of the signal generating molecules. But such approach suffers: (i) the nanoparticle can block the signal, (ii) due to the nanoparticles' size, only limited number of nanoparticles can be used, hence limiting the detectable analyte's concentration, and (iii) just like a car tire having a small portion in contract with the ground, only a small portion of the nanoparticles can be near the analytes to be effective, while the rest parts of the nanoparticle prevent the analytes under them from contacting nanoparticles.

Sensing Amplifying Layer (SAL)

The SAL 201 comprises a layer of nanostructures made of metallic materials and dielectric/semiconductor materials, that can enhance the signal. Often the outer surface of the SAL (the inner surface of SAL is the surface in contact with the substrate surface) is coated with a molecular adhesion/spacer layer, which serves one of the two or both of the functions: (1) provide a good adhesion to bond to the capture agents, and (2) a spacer that control the distance between the metal in the SAL and the signal generation molecule to optimize signal amplification. One preferred SAL embodiment is that the dimension of one, several or all critical metallic and dielectric components of SAL are less than the wavelength of the light in sensing.

Examples for SAL structures—1

One embodiment of the sensing implication surface comprises a or a plural of metallic discs and a significantly continuous metallic film, wherein a substantial portion of the metallic disc has a separation from the metallic film, and the separation and the dimensions of the disks are less than the wavelength of the light used in sensing.

Several examples of the embodiments 400, shown in FIG. 12, comprises substrate 410, substantially continuous metallic film 420, one or a plurality of pillars extending from a surface of the substrate, wherein at least one of the pillars comprises a pillar body 420, metallic disc 430 on top of the pillar, and metallic back plane 450. The metallic back plane can be either type A 451: at the foot of the pillar covering a substantial portion of the substrate surface near the foot of the pillar; or type B 452: a sheet of film go under the pillar. The discs can have a lateral dimension either larger (preferred) or smaller or the same as the pillars.

In one embodiment for sensing using the light wavelength of 400 nm to 1,000 nm (visible to near-infra-read), the separation is 0.5 to 30 nm, and the average disc's lateral dimension is from 20 nm to 250 nm, depending upon the light wavelength used in sensing. One example of such embodiment is shown in FIG. 12. The metallic disk in all embodiments has a shape selected from the group of shapes consisting of round, polygonal, pyramidal, elliptical, elongated bar shaped, or any combination thereof.

Another embodiment of the sensing implication surface comprises a or a plural of metallic discs on a substrate and the average disc's lateral dimension of from 20 nm to 250 nm, and has at least a gap of 0.5 to 30 nm between the two adjacent discs.

Examples for SAL structures—2: D2PA

With reference to FIG. 13, a D2PA plate is a plate with a surface structure, termed "disk-coupled dots-on-pillar antenna array", (D2PA), 100 comprising: (a) substrate 110; and (b) a D2PA structure, on the surface of the substrate, comprising one or a plurality of pillars 115 extending from a surface of the substrate, wherein at least one of the pillars comprises a pillar body 120, metallic disc 130 on top of the pillar, metallic back plane 150 at the foot of the pillar, the metallic back plane covering a substantial portion of the substrate surface near the foot of the pillar; metallic dot structure 140 disposed on sidewall of the pillar. The D2PA amplifies a light signal that is proximal to the surface of the D2PA. The D2PA enhances local electric field and local electric field gradient in regions that is proximal to the surface of the D2PA.

The light signal includes light scattering, light diffraction, light absorption, nonlinear light generation and absorption, Raman scattering, chromaticity, luminescence that includes fluorescence, electroluminescence, chemiluminescence, and electrochemiluminescence.

General Shapes and Dimensions. In some embodiments, the dimensions of one or more of the parts of the pillars or a distance between two components may be that is less than the wavelength of the amplified light. For example, the lateral dimension of the pillar body 120, the height of pillar body 120, the dimensions of metal disc 130, the distances between any gaps between metallic dot structures 140, the distances between metallic dot structure 140 and metallic disc 130 may be smaller than the wavelength of the amplified light. In some embodiments, the metallic dots are not used, just the metallic disks and the metallic backplane separated by a gap.

As illustrated in FIG. 13, the pillars may be arranged on the substrate in the form of an array. In particular cases, the nearest pillars of the array may be spaced by a distance that is less than the wavelength of the light. The pillar array can be periodic and aperiodic.

Pillars for all SALs with pillars. The pillar bodies on the top layer of the substrate may be formed from an insulating material, but may be semiconductors. Exemplary materials for the formation of the pillars are dielectrics: silicondioxide, silicon-nitride, hafnium oxide (HfO), Aluminum oxide (AlO) or semiconductors: silicon, GaAs, and GaN. Once formed, the pillars may have sidewalls which are columnar (straight), sloped, curved, or any combination thereof. The shape of the top surface of the pillar can be round, a point (of a pyramid), polygon, elliptical, elongated bar, polygon, other similar shapes or combinations thereof. The height of each pillar may be chosen from 5 nm to 300 nm.

The lateral dimension of each pillar should be less the amplified light wavelength, and should be chosen from 5 nm to 8,000 nm, according the amplified light wavelength. The spacing between the pillars in the array can be periodic or aperiodic. The preferred spacing should be less than amplified light wavelength. For some applications, a periodic period is preferred and the period is chosen to maximize the light absorption and radiation, which is light wavelength dependent. The spacing (pitch) between adjacent pillars in the array may be from 4 nm to 4000 nm.

Metallic disc for all SALs with metallic discs. The metallic disc array can be periodic and aperiodic. The metallic disc on the top of each pillar can have a shape of rounded, pointed (as in the form of a pyramid or cone), polygonal, elliptical, elongated bar, polygon, other similar shapes or combinations thereof. Each disk may have the same, similar or different shapes with the other disks. The metallic disc lateral dimension and thickness should be less than the light amplified wavelength. Depending upon the amplified light wavelength, a lateral dimension of each disc can be chosen from 4 nm to 1500 nm, and a thickness of the disc is from 1 nm to 500 nm. The preferable metallic material thickness for the light wavelength range of 400 nm to 1100 nm is from 5 nm to 80 nm. For using different metallic material thickness, the pillar height needs to adjusted to achieve the intend gap between the disks and the back plane. The shape of each disc can be the same as, smaller, or larger, or different from, the shape of the top surface of the associated pillar on which it is disposed. The shape difference can be various from 0 to 200 nm depending the working wavelength.

Metallic backplane for all SALs: The metallic backplane works together with the metallic disks to form a light cavity. In the embodiment, the metallic back plane defines a metallic layer on the substrate with a hole for each pillar. The hole size should be less than the amplified light wavelength. The thickness of the metallic back plane is selected to be from 1 nm to 2000 nm, with a thickness in the range of 10 nm-200 nm preferred. The material of the metallic back plane can be selected from the same group as is used to form the metallic disc described above, but for a given D2PA structure, the metallic back plane can be formed from either the same or a different material as that used to form the discs. The D2PA nanodevice of any prior claim, wherein said pillar has a sidewall surface that is columnar, sloped, or curved.

Metallic dots for all SALs with metallic dots. Disposed on the sidewalls of each pillar between the metallic disc and the metallic back plane, the metallic dots have shapes which are approximately spherical, discs-like, polygonal, elongated, other shapes or combinations thereof. The metallic dots on a pillar may all have approximately the same shape, or may be individually varied. The dimensions of the metallic dots should be smaller than the amplified light wavelength, and are, depending the amplified light wavelength, preferably between 3 nm to 600 nm, and may be different in three dimensions. In some embodiments, the gaps between the neighboring metallic dots and the gap between the disc and adjacent metallic dots is between 0.5 nm to 200 nm. For many applications, a small gap is preferred to achieve a stronger enhancement of the signals. The gaps may be varied between each metallic dot on a pillar.

Metallic materials for all SALs: The metallic materials for the metallic disks, backplanes, and dots are chosen from (a) single element metal, such as gold, silver, copper, aluminum, nickels; (b) a combination of the multiplayer and/or multilayer of the single metals; (c) metallic alloys; (d) semiconductors, (e) any other materials that generate plasmons at the amplified light wavelength, or (f) any combination of (a), (b), (c), (d) and (e). Each of the metallic disks, backplane, and dots use the same metallic materials as the others or different metallic materials.

Substrates for all SALs. The substrate offer physical support to the D2PA and should be any materials, as long as it does not generate chemical and electromagnetic interference to the D2PA amplification. The substrate also can be in many different forms: thin film (membrane) and thick plate, flexible and rigid. The substrate may be made of a dielectric (e.g., $SiO_2$) although other materials may be used, e.g., silicon, GaAs, polydimethylsiloxane (PDMS), poly(methyl methacrylate) (PMMA).

Preferred D2PA embodiments for light wavelength (400 to 1000 nm) in visible and near-infra-red. All dimensions of the critical elements of D2PA are less the wavelength of the light. The metallic materials are selected from gold, silver, cooper, and aluminum and their alloys. In one embodiment that is configured for enhance light at a wavelength of ~800 nm, the D2PA nanostructure may be composed of a periodic non-metallic (e.g. dielectric or semiconductor) pillar array (200 nm pitch and ~100 nm diameter), a metallic disk on top of each pillar, a metallic backplane on the foot of the pillars, metallic nanodots randomly located on the pillar walls, and nanogaps between these metal components. The metallic disk has ~120 nm diameter and is slightly larger than the diameter of the pillar, hence having an overhang. The disk array and the backplane (both are 40 nm thick) form a 3D cavity antenna that can efficiently traps the excitation light vertically and laterally. The height of the pillar is ~50 nm and hence the nearest distance between the metallic disk and the metallic backplane is about 10 nm. The nearest distance, often termed "nanogap", is preferred as small as possible for a higher enhancement.

Each pillar has about 3 to 30 nanodots depending upon the pillar geometry and fabrication processing conditiona; and the pillar density is $2.5 \times 10^9$ pillars/cm$^2$. The preferable metallic material thickness for this light wavelength range is from 5 nm to 80 nm. For using different metallic material thickness, the pillar height needs to adjusted to achieve the intend gap between the disks and the back plane. Again, in some embodiments, the metallic dots are not used, just the metallic disks and the metallic backplane separated by a gap.

Examples for the spacer thickness: The thickness of the spacer, that separate the metal from the molecules that generate optical signal, is from 3 nm to 50 nm for fluorescence (preferred for 5 nm for ~800 nm light wavelength); and 1 to 15 nm for surface enhanced Raman scattering (SERS). The thickness depends the wavelength of light.

Molecular Adhesion Layer and Attachment of Capture Agents

In one embodiment, there is a molecular adhesion layer (also termed "molecular linking layer") (MAL) between the SAL and the capture agents. The molecular adhesion layer serves two purposes. First, the molecular adhesion layer acts a spacer. For optimal fluorescence, the light-emitting labels (e.g., fluorophores) cannot be too close to the metal surface because non-radiation processes may quench fluorescence. Nor can the light-emitting labels be too far from the metal surface because it may reduce amplification. Ideally, the light-emitting labels should be at an optimum distance from the metal surface. Second, the molecular adhesion layer provides a good adhesion to attach capture agent onto the SAL layer. Adhesion is achieved by having reactive groups in the molecules of the molecular adhesion layer, which have a high affinity to the capture agent on one side and to the SAL layer on the other side.

The molecular adhesion layer can have many different configurations, including (a) a self-assembled monolayer (SAM) of cross-link molecules, (b) a multi-molecular layers thin film, (c) a combination of (a) and (b), and (d) a capture agent itself.

Various method for linking capture agents to a metal surface, with or without a molecular linking layer, are described in WO2013154770, which is incorporated by reference for such methods. For example, in some cases, the metal surface may be first joined to one end (e.g., via a thiol or silane head group) of a molecule of a defined length (e.g., of 0.5 nm to 50 nm in length) and the capture agent can be linked to the other end of the molecule via a capture agent-reactive group (e.g., an N-hydroxysuccinimidyl ester, maleimide, or iodoacetyl group). Dithiobis(succinimidyl undecanoate), which has a —SH head group that binds to a gold surface through sulfer-gold bond, and an NHS-ester terminal group that reacts with primary amines, may be used in certain cases.

Container. The plate with SAL may be disposed within a container, e.g., a well of a multi-well plate. The plate with SAL also can be the bottom or the wall of a well of a multi-well plate. The plate with SAL may be disposed inside a microfluidic channel (channel width of 1 to 1000 micrometers) or nanofluidic channel (channel width less 1 micrometer) or a part of inside wall of such channels.

Signals and Pixelated Reading

The signal above can directly come from the analyte or a label attached to the analyte, or the combination. The signal is electromagnetic signal, including electrical and optical signals with different frequencies, light intensity, fluorescence, chromaticity, luminescence (electrical and chemoluminescence), Raman scattering, time resolved signal (including blinking). The signals also can be the forces due to local electrical, local mechanical, local biological, or local optical interaction between the plate and the reading device. The signal also includes the spatial (i.e. position), temporal and spectral distribution of the signal. The detection signal also can be absorption.

In optical detection (i.e. detection by electromagnetic radiation), the methods that can be used include far-field optical methods, near-field optical methods, epi-fluorescence spectroscopy, confocal microscopy, two-photon microscopy, and total internal reflection microscopy, where the target analytes are labelled with an electromagnetic radiation emitter, and the signal in these microscopies can be amplified by the SML.

The reading will use appropriate detecting systems for the signal to be detected in sequence or in parallel or their combination. In a sequential detection, one or several pixels are detected a time, and scanner will be used to move the detection into other areas of the SAL. In a parallel detection, a multipixel detector array, such as imaging camera (e.g. CCD's), will be used to take detect the signals from different pixels at the same time. The scan can be single path or multi-path with a different pixel size for each path. FIG. 2C schematically illustrates pixelated reading on an x, y, z stage.

The pixel size for the reading/detection will be adjusted to for the balance of optical resolution and total reading time. A smaller pixel size will take a longer time for reading/scanning the entire or fraction of the SAL. A typical pixel size is 1 um to 10 um in size. The pixel has different shapes: round, square and rectangle. The lower limit of the pixel size is determined by the optical resolution of the microscope system, and the higher limit of the pixel size is determined in order to avoid reading error from the uneven optical response of the imager (optical aberration, illumination uniformity, etc.).

Reading System

A reading system comprise (a) a plate comprises a sensing amplification layer comprises nanostructures that enhance signals and the capture agents are attached to said amplification layer 200; (b) a reading device 205 for producing an image of signals emanating from a surface of said plate, wherein signals represent individual targeted analyte binding events; (c) a device assembly 300 that holds the plate and the imager; (d) an electronics and a data storage 301 for storing said image; and (e) a computer comprising programming for identifying and counting individual binding events in an area of the image.

The device assembly 300 controls or changes the relative position between the plate and the reading device, in at least one of the three (x, y, z) orthogonal directions, for reading the signal. The device assembly can include a scanner 301. The scanner 301 can scan in in at least one of the three (x, y, z) orthogonal directions. The reading device 302 is a CCD camera. The reading device 302 also can be a photodetector comprising one or more other optical devices that are selected from optical filters 303, spectrometer, lenses 304, apertures, beam splitter 305, mirrors 306, polarizers 307, waveplates, and shutters. The reading device collects the position, local intensity, local spectrum and local Raman signature of said signals.

For examples, for optical signal detection, optical filters 303, light beam splitters 305, optical fibers, a photodetector (e.g. PMT, APD), imaging camera (e.g. CCD's) and spectrometer together with a scanner provided by the device assembly 301 can be coupled to a microscope system which uses a far-field confocal setting or a wide-field view setting.

Figure 9:
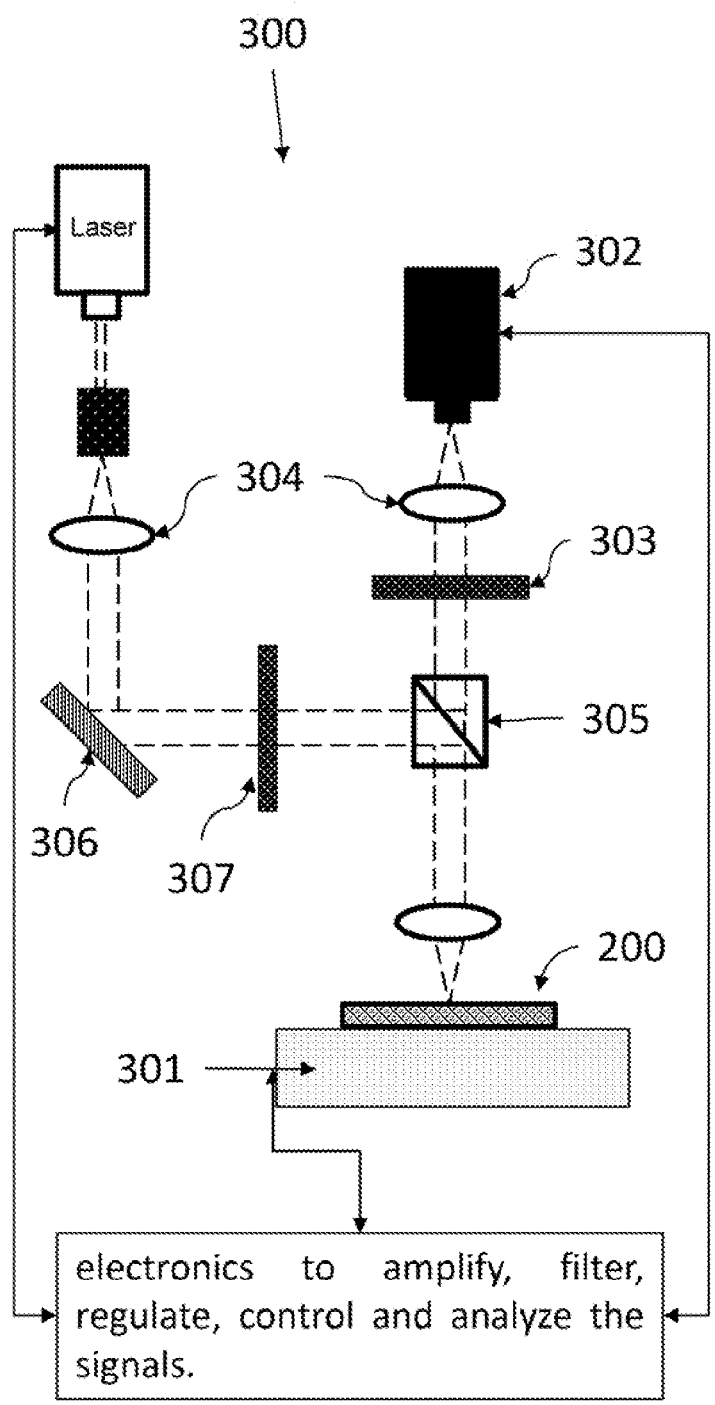
FIG. 9 schematically illustrates the detection/probing system for performing pixel reading method.
Figure 10:
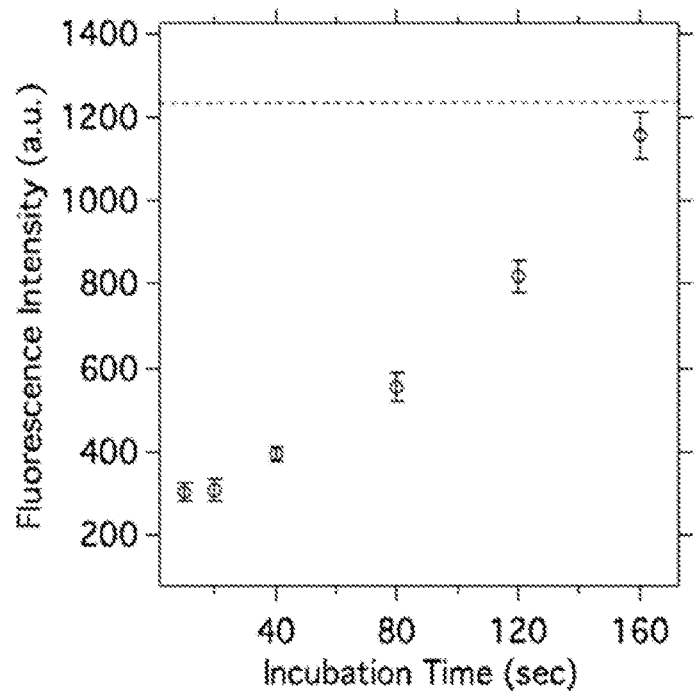
FIG. 10 is a graph showing fluorescence intensity of 10 pM immunoassay incubated in DC field within 160 s. The dashed line is the fluorescence signal intensity of the identical immunoassay performed without DC-field and using 1 hour incubation time.

In confocal setting, the reading is performed by recording the 's brightness, temporal change and spectral change of one or a few pixels a time and raster scanning the entire interested area of the SAL. In wide-field view setting, a camera is used to record the brightness and temporal change of the entire or a fraction of SAL area a time. Proper optical filters and light beam manipulators (polarizer, beam splitters, optical fibers, etc.) is need to ensure only the desired signal is collected and detected. FIG. 9 schematically illustrates one arrangement of components for this system.

Pixelated Analysis

The signals detected in a pixelated manner are analyzed to determine the number and/or types of the particular molecules at a particular pixel or several pixels, which, in turn is used to quantify the type and/or concentration of the targeted analytes.

Figure 5:
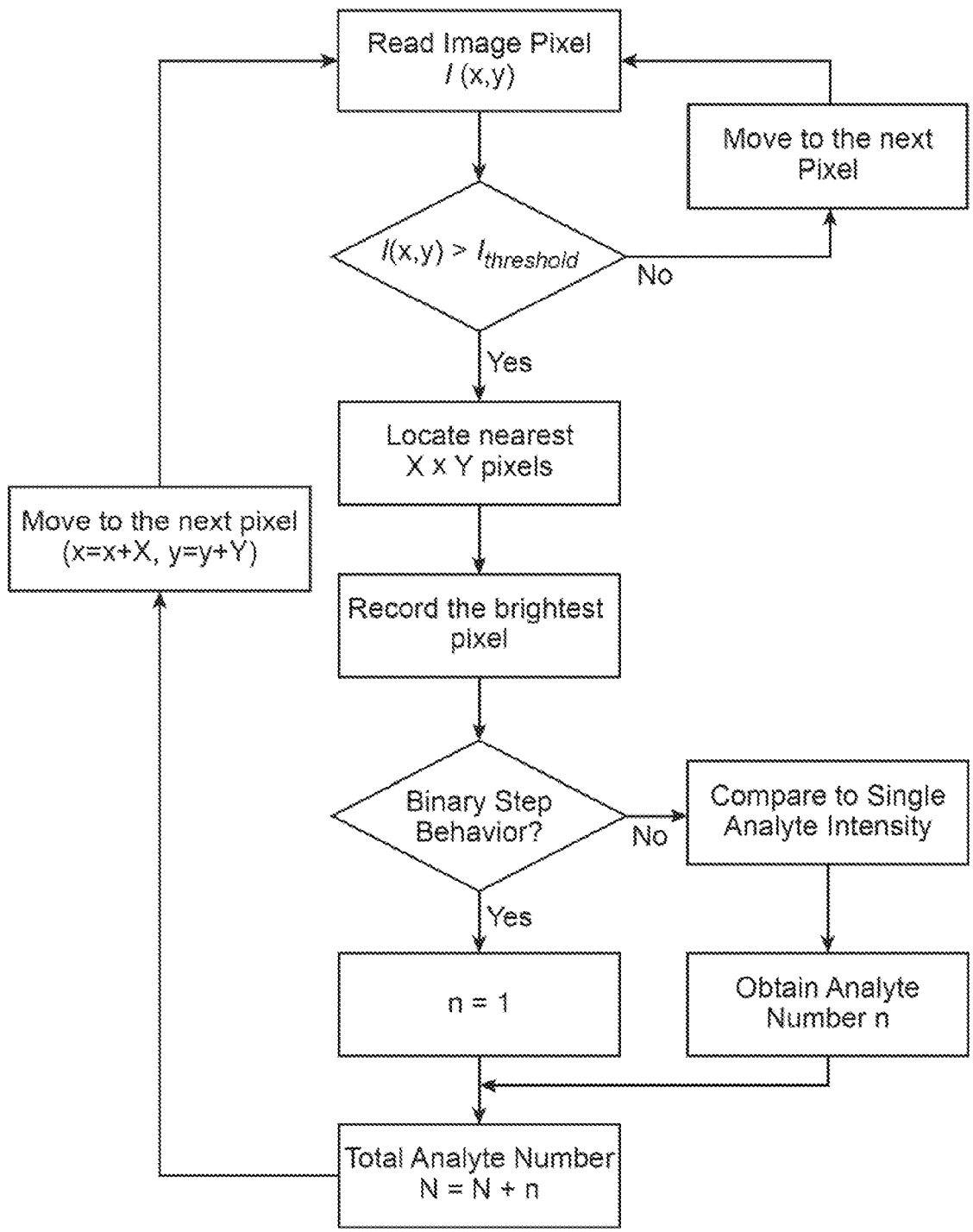
FIG. 5 shows a flow chart for an algorithm of finding analyte numbers using the pixel assay.

The analysis include to analyze the spatial, tempo, spectral information of the signal. The analysis include statistical analysis, comparison, integration, and others. FIG. 5 shows a flow chart for one embodiment of this method. Some examples of the analysis are provided below.

The analysis method—1 includes (1) determine the local background signal intensity, (2) determine local signal intensity for one label, two labels, etc.; and (3) determine the total number of labels in the imaged area.

The background signal means the signal that is generated under the exact conditions as other samples, except that the sample does not contain any targeted analytes.

Analysis-1 is based on using EM-CCD to record the spatial distribution bioassay signal intensity. It is used when discrete hot spot (bright pixels) on D2PA sensors are imaged.

(1) Determine the local background signal intensity. To determine the background signal, a reference sample is used. This reference sample is a D2PA sensor without any analyte immobilized and is imaged using the identical instrumentation set at identical experiment conditions for bioassays on D2PA. The intensities of all the pixels of the image are then plotted in a histogram, which gives the number of pixels at certain signal intensity. The signal intensity with the most corresponding pixel numbers is then determined as the background signal Background. This background intensities, together with their standard deviation (s.d.), is used to determine the threshold value defined to differentiate local background and local hot spot, which is Threshold=Background+n*s.d. Here n is an integer number used as a parameter to adjust the threshold value. Usually, n is set equals to 3, 5, or 7 in this work.

(2) For single bright pixel ($I_{x,y}$>Threshold), the local signal intensity of labels are determined using a two-step procedure. First, time-evolved imaging of a sample is used to find hot spot that has single labels (analyte). The total time of imaging is on the scale of 10s of seconds and the resolution is on the scale of 10s of milli-second. For hot spot of single analyte, a clear ON/OFF binary behavior of hot spot fluorescence intensity is observed. The pixels that displays such behavior are first counted as single labels/analyte. Their coordinate on the image and intensity is thus recorded. The averaged intensity of these hot spot is then used as the brightness of single label on D2PA assay.

Second, Bright pixels that does not show such binary behavior thus indicates multiple labels/analyte. We then compare their signal intensity to average brightness of single label to count the number of labels in local hot spot. Alternatively, another simplified procedure is utilized based on Poisson statistics principle. At low concentration of analyte (<1 pM), the probability of small amount of analyte immobilized in the high density of plasmonic hot spot ($\sim 2.5 \times 10^7$ mm$^{-2}$) observes Poisson distribution, which means the probability of more than two analyte being located in the same plasmonic hot spot is low. For example, at 1 fM of target analyte, the probability of more than two labels located within our imaging area, which contains more than 56,250 D2PA structures, is less than 0.01% (estimated). Therefore, it can be assumed that all bright hot spots that does not show single label behavior contains only two labels.

(3) After finishing (1) and (2), a list of hot spot pixel coordinates, intensities and corresponding label numbers can then be tabulated. The total number of labels can be obtained by SUM over the label numbers of each bright pixel.

The analysis-2 method includes (1) determine the local background signal spectrum, (2) determine local signal spectrum for one label, two labels, etc.; and (3) determine the total number of labels in the imaged area.

Analysis-2 is based on using high-resolution spectrometer combined with a confocal microscope setup to record spatial distribution of bioassay signal spectra.

(1) To determine the background signal, a reference sample is used. This reference sample is a D2PA sensor without any analyte immobilized and is imaged using the identical instrumentation set at identical experiment conditions for bioassays on D2PA. A confocal microscope is then used to measure the local bioassay signal spectrum. The detection area is determined by the pin-hole size before the high-resolution spectrometer and the numerical aperture of the microscope objective lens. The confocal microscope raster scan the entire D2PA sensor to obtain the spatial distribution of background signal spectrum I(x,y,λ). A histogram is then plotted which gives the number of pixels with a certain spectrum moment ($\int I(\lambda)d\lambda$). Similarly to analysis-1 step (1), the spectrum moment with the most pixels are used as the background signal and their standard deviation is used to determine the threshold value: $I(\lambda)_{threshold}=I(\lambda)_{background}+n*s.d.(\lambda)$. Here n is an integer number used as a parameter to adjust the threshold value. Usually, n is set equals to 3, 5, or 7 in this work. (2) To collect the spectrum of a single bright pixel, a confocal microscope setup coupled to a high resolution spectrometer is used. Read-out is performed similar to step (1). Since spectrum of a single molecule can only be reliably detected using high-sensitivity CCD with seconds of exposure time, which cannot provide enough time resolution to determine single labels' binary behavior in a hot spot. Thus to determine the number of labels at a bright pixel, we will compare the spectrum moment between different bright pixels. Due to the large amplification of D2PA sensor, single or multiple labels can be differentiated from background. Thus the number of analytes within the hot spot can be determined.

(3) After finishing (1) and (2), a list of hot spot pixel coordinates, spectrum moments and corresponding label numbers can then be tabulated. The total number of labels can be obtained by SUM over the label numbers of each bright pixel.

The analysis-3 (Sensing by Pixelated SERS signal) includes (1) determine the local background signal of "surface enhanced Raman scattering" (SERS) signature, (2)

determine local SERS signal for one label, two labels, etc.; and (3) determine the total number of labels in the imaged area.

Analysis-3 is based on using high-resolution spectrometer combined with a confocal microscope setup to record spatial distribution of bioassay signal SERS spectra.

(1) To determine the background signal, a reference sample is used. This reference sample is a D2PA sensor without any analyte immobilized and is imaged using the identical instrumentation set at identical experiment conditions for bioassays on D2PA. A confocal microscope is then used to measure the local bioassay SERS spectrum. The detection area is determined by the pin-hole size before the high-resolution spectrometer and the numerical aperture of the microscope objective lens. The confocal microscope raster scan the entire D2PA sensor to obtain the spatial distribution of background signal spectrum $I(x,y,cm^{-1})$. For a certain biomoleucle, a histogram is then plotted which gives the number of pixels with the molecule's unique SERS signature intensity $I(cm^{-1})$. Similarly to analysis-1 step (1), the spectrum moment with the most pixels are used as the background signal and their standard deviation is used to determine the threshold value: $I(cm-1)threshold=I(cm^{-1})$ background+n*s.d$(cm^{-1})$. Here n is an integer number used as a parameter to adjust the threshold value. Usually, n is set equals to 3, 5, or 7 in this work.

(2) To locate local hot spot, a confocal microscope setup is used to raster scan the entire D2PA sensor in a way similar to (1). Unlike analysis-1 or analysis-2, SERS is label free detection method and the single molecule SERS signal does not show binary behavior. Thus to determine the number of labels at a bright pixel, we will compare the SERS signature $I(cm^{-1})$ between individual bright pixel. Due to the large amplification of D2PA sensor, single or multiple analyte can thus be differentiated from background. The number of analytes within the hot spot can then be determined.

(3) After finishing (1) and (2), a list of hot spot pixel coordinates, SERS signature intensity and corresponding label numbers can then be tabulated. The total number of labels can be obtained by SUM over the label numbers of each bright pixel.

EXAMPLES

Aspects of the present teachings can be further understood in light of the following examples, which should not be construed as limiting the scope of the present teachings in any way.

Example—1

Single-molecule Emitters on Plasmonic Nanostructures and Observation of Blinking Event We measured the fluorescence enhancement of the immunoassay from a single labeled IgG molecule which was placed at a "hot spot" of D2PA (namely the region where the local electric field is the strongest). Such single molecule fluorescence can be visible when the IgG molecules are far apart from each other (i.e. a very low IgG concentration) and a sensitive CCD camera is used.

Particularly, we used an IgG concentration of 100 pM to study single molecule fluorescence, which gives an average distance between two immobilized IgG about 420 nm. We mapped the two-dimensional fluorescence of the immunoassay using an inverted microscope (Nikon, USA) with 40× objective lens (N.A.=0.6). A 785 nm laser beam was expanded uniformly to illuminate a 50 μm×50 μm area on D2PA plates. Images were continuously collected by an electron multiplying charge-coupled device (EM-CCD, Andor) of 512×512 pixel resolution (hence ~390 nm per pixel for the given laser scanning area). The CCD pixel size oversamples the fluorescence intensity distribution imaged at optical diffraction-limit (0.8 μm determined by Rayleigh criterion).

Figure 6:
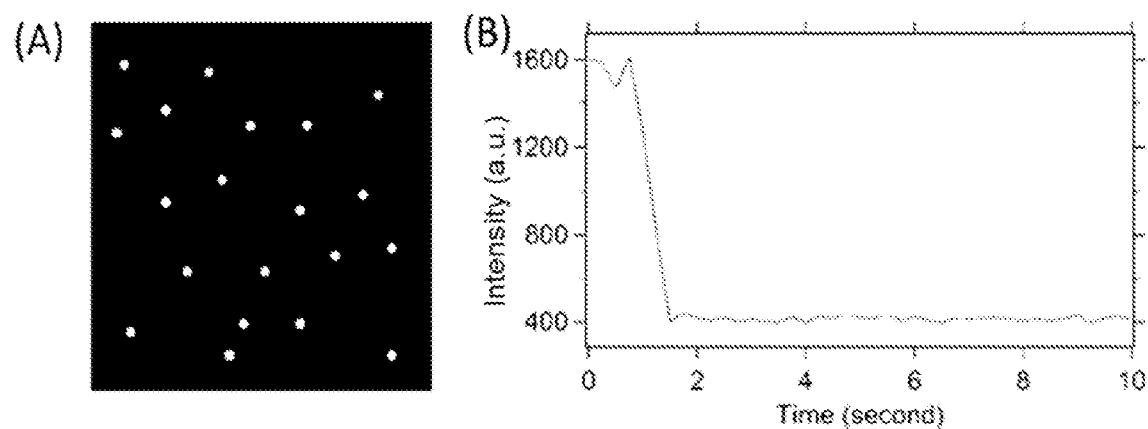
FIG. 6: (A) Illustration of an example pixel read-out 2D image of fluorescence assay on SAL. (B) Temporal fluorescence intensity dependence of bright pixel, the binary ON/OFF behavior indicates the bright pixel only contains single molecule.

From the fluorescence imaging of 100 pM fluorescent-labeled IgG on D2PA plate, we observed distinct fluorescence "bright spots" that were randomly distributed in a uniform background (FIG. 6A). The fluorescence intensity of individual bright spot as a function of time was shown to have a binary stepwise behavior (blinking event) (FIG. 6B), which indicates that a single molecule at or near a D2PA's hot spot first emits fluorescence and then gets bleached (blink-off).

To estimate the fluorescence enhancement factor for single molecule at a hot spot, $g_{Hotspot}$, we used two methods. For method-1, $g_{Hotspot}$ is the ratio of the single molecule fluorescence signal at a "hot spot" of D2PA, $S_{Hot.spot}$, to the average fluorescence signal per molecule on reference sample (which equals to the area-average fluorescence intensity on reference sample, $I_{Ref.Avg}$, divided by the average IgG molecules per unit area on reference sample, $n_{Ref.Avg}$). According to FIG. 6(a), $S_{Hotspot}$=1,200 counts, $I_{Ref.Avg}$=3,088 counts/μm2, and $n_{Ref.Avg}$=7.22×105 molecule/μm2, $I_{Ref.Exc}$=1.74 mW and $I_{Exc.D2PA}$=110 μW. We found the fluorescence enhancement is $g_{Hotspot}$=4.4×10$^6$, which is 3 orders of magnitude larger than most of the reported fluorescence enhancement for a single molecule in the "hot spot".

For the second method, the average fluorescence intensity per molecule for the reference was deducted from the average fluorescence intensity per molecule for the D2PA plate ($I_{D2PA.Avg}/n_{D2PA.Avg}$) divided by the fluorescence enhancement factor (EF). For $I_{D2PA.Avg}$=19 counts, EF=7, 220 and $n_{Avg}$~7.22 molecule/μm2, we found $g_{Hotspot}$=3.28× 10$^6$. Both methods gave consistent results for calculating the single molecule fluorescence enhancements. The average of the two methods gives $g_{Hotspot}$ ~4×10$^6$.

Example—2

Digital Counting of Blinking Single-molecule Emitter

In an immunoassay performed on D2PA sensor, if a biomarker is located on a LSP hot spot, its fluorescence signal will be enhanced by 4×106 fold, allowing single molecule detection sensitivity using a CCD camera. Such enhancement of a single emitter from LSP hot spot is uniformly distributed over a large area, e.g., wafer size, with high density, thus enabling us to calculate single-molecule emitter concentration from their surface distributions on D2PA surface.

At low concentration (<1 pM), the ratio of biomarker number (and the resulting fluorophore number) to the D2PA nanopillars is very small, thus a single D2PA nanopillar can have only one fluorophore or none. For nanopillars that have single fluorophore, the high density of plasmonic hot spot on each D2PA nanopillars ensures the fluorescence signal will be amplified and detectable regardless of the exact location of the single molecule on the pillar. Thus the D2PA can offer single molecule signal map over the entire sensor surface.

The new method is measured using a standard inverted microscope imaging system equipped with a scanning semiconductor laser. The excitation laser is chosen based on the plasmonic resonance of D2PA and absorption spectrum of chosen fluorescence label. The laser beam is raster scanning over the entire field of view (FOV) of the microscope objective lens by using a 2D scanning Galvo mirror system. For this report, the FOV is 200 um×200 um.

Our method includes these steps:
  Under the inverted microscope, take time-serial fluorescence imaging of the D2PA sensor surface, which shows scattering distribution of fluorescence hot spots in the FoV, and their time-dependent fluorescence intensities.
  Translate the XY stage of the inverted microscope to the nearby area and repeat step 1 until the entire D2PA sensor surface (3 mm×3 mm) is imaged. The entire sensor surface needs to be imaged instead of only sampling a few individual images because at extreme low concentration (<10 aM), not every individual image has detectable fluorescence hot spot.
    To count only the single-molecule emitter, we only count the hot spot if they demonstrate blinking event. This is achieved by looking each hot spot's fluorescence intensity over time- a binary step behavior is a characteristic behavior for single-molecule emitters.
    For high analyte concentrations (>1 pM), the hot spots on the surface are too close to be differentiate from each other. Counting is thus not appropriate. In this case, total fluorescence intensity is obtained by integrate over the entire sample surface.
    For lower concentration, counting is possible since hot spots are scarcely distributed. In this case, total hot spots number is obtained by summing hot spots count from all the images.
  Plot the response curve (signal as a function of analyte concentration). Use integrated fluorescence intensity signal for higher concentration and total hot spot number as signal at lower analyte concentration.

By only counting the fluorescence hot spot number (from either the biomarkers or the non-specific bonded molecules), the noise from the CCD background read ICCD can be ruled out. ICCD becomes dominant in conventional immunoassay at extreme low concentrations. Therefore, the background signal and its standard deviation a is significantly reduced. In the new method, the background noise comes only from the non-specific bonded molecules, which can be further minimized by proper washing, blocking and choice of detection antibodies. In addition, counting the fluorescence hot spot intrinsically has smaller signal standard deviation compared to measuring the fluorescence intensity because it neglects the signal difference between individual hot spots.

Example—3

Digital Counting of Breast Cancer Biomarker CEA Immunoassay

As a demonstration, we detect clinically relevant cancer biomarker CEA and obtained a detection sensitivity down to 10-19M. Preparation of CEA immunoassay on D2PA nanodevice. The D2PA immunoassay plate consists of two components: (1) the aforementioned D2PA plasmonic nanostructure and (2) a mixed self-assembled layers of Protein A layer on top of ithiobis succinimidyl undecanoate (DSU). The DSU molecules provide strong cross-link of protein A to gold surface by providing one end of sulfide that strongly binds to gold and the other end of N-hydroxysuccinimide (NHS) ester group that binds well to Protein A's amine group. These molecular layers (Protein A and DSU) have two functions: (1) with a combined thickness of 6.5 nm, they will act as a spacer layer that can suppresses metal's fluorescence quenching effect and (2) Since antibodies will bind to protein A through their Fc region, the molecule layers on D2PA can increase the quality of antibody orientation and immobilization, which will further improve the capture efficiency of the antibodies.

Figure 11:
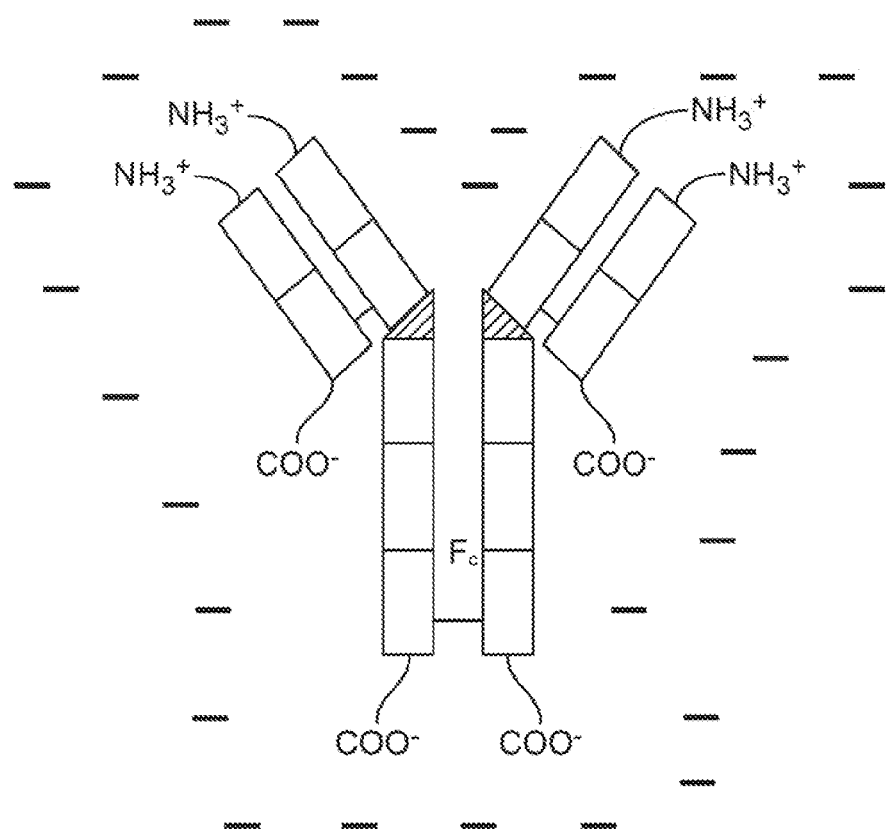
FIG. 11: Under a certain voltage bias, the electric field and electric field gradient can help the attachment and alignment of analytes, which in turn can improve sensing sensitivity. (a) A negatively charged IgG. Though the overall charge is negative, the charge distribution on the antibodies is not uniform. (b) Schematics of the electrochemical deposition of oriented antibodies. The Au electrode is functioned with DSU monolayer.
Figure 11:
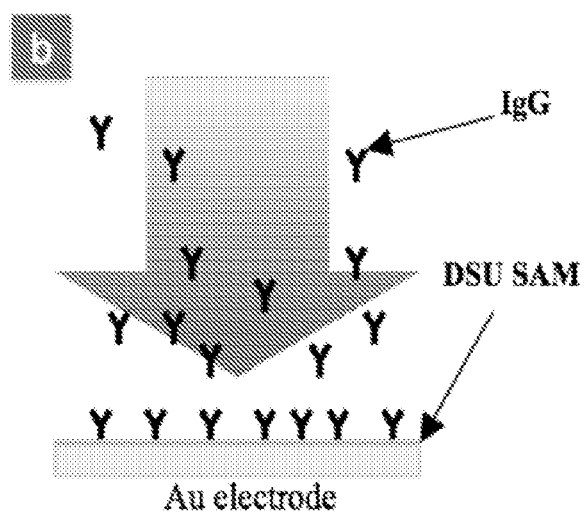

For coating DSU SAM and Protein A on the D2PA, freshly fabricated D2PA substrate was first diced into 5 mm×5 mm pieces and immersed in a solution of 0.5 mM DSU (Dojindo, Japan) in 1,4-dioxane (Sigma-Aldrich), and incubated overnight at room temperature in a sealed container. After incubation, the D2PA substrates were rinsed extensively in 1,4-dioxane and dried with argon gas. We immediately place these DSU coated D2PA substrates in separated wells of a standard 96-well plates (Pierce, USA). They were then immersed in 100 uL of 10 ug/mL Protein A (Rockland Immunochemicals) in phosphate buffered saline (PBS) solution (pH=7.2, Sigma-Aldrich) and incubated in a sealed condition overnight in the fridge at 4 C. We then aspirate the solution and wash each individual D2PA plates 3 times in washing solution (R&D systems) for 15 minutes each to remove the unbonded protein A. The plates were then gently rinsed in streams of deionized water to remove any salt content. After drying with argon gas, the D2PA immunoassay plate was ready for immediate immunoassay testing or stored at −20 C. degree for later use. As shown in FIG. 11, in certain cases antibodies can be moved to the DSU SAM using an electric field.

Figure 7:
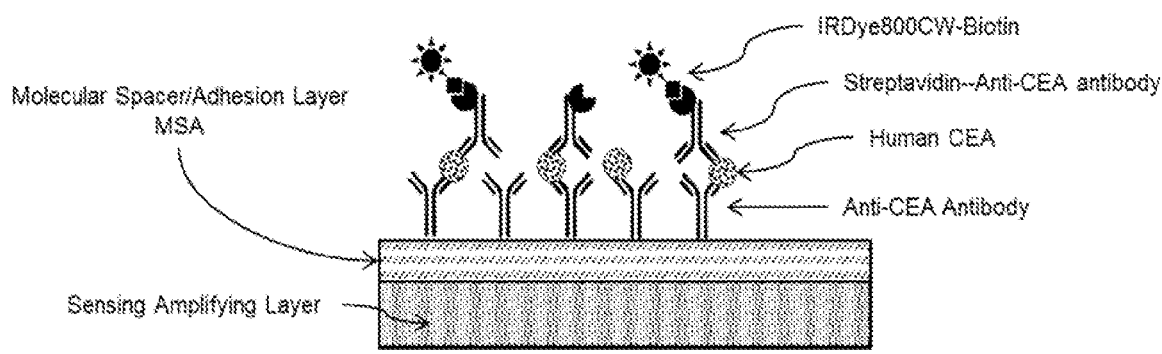
FIG. 7 is a schematic illustration of an exemplary immunoassay showing a four-layer sandwich immunoassay of human CEA cancer biomarker.
Figure 8:
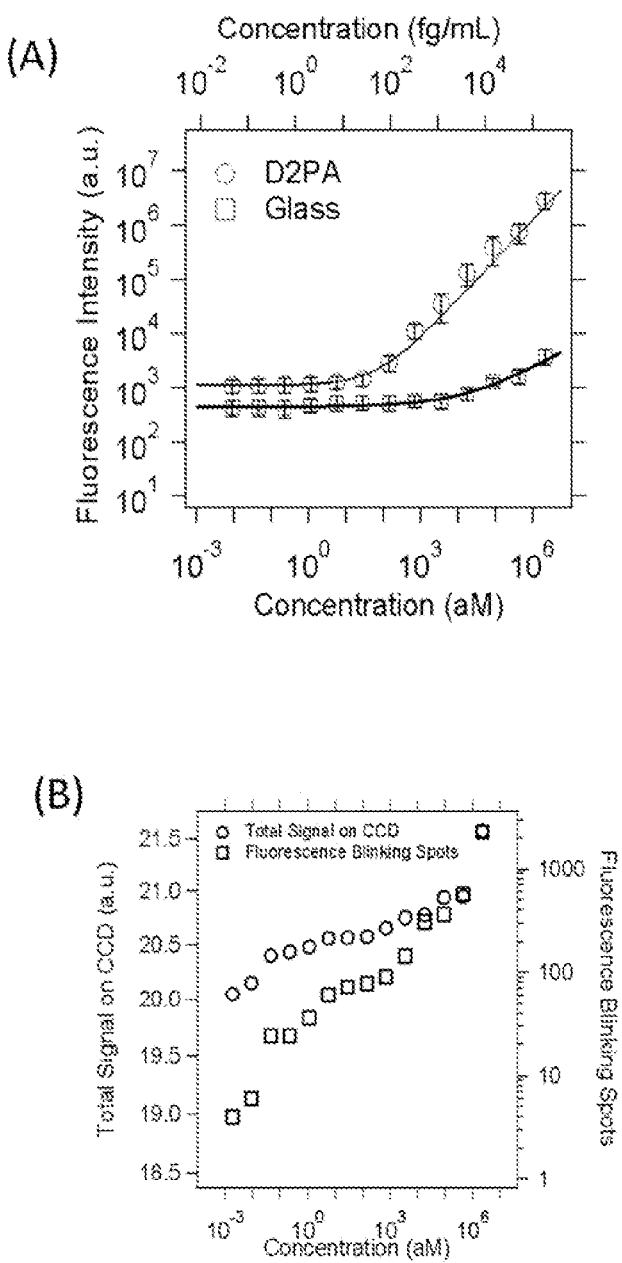
FIG. 8 shows histogram of bright pixels number as a function of their signal intensity at different CEA analyte concentrations. The bright pixel number is normalized to the total plasmonic hot spot number within the detection area.
Figure 8:
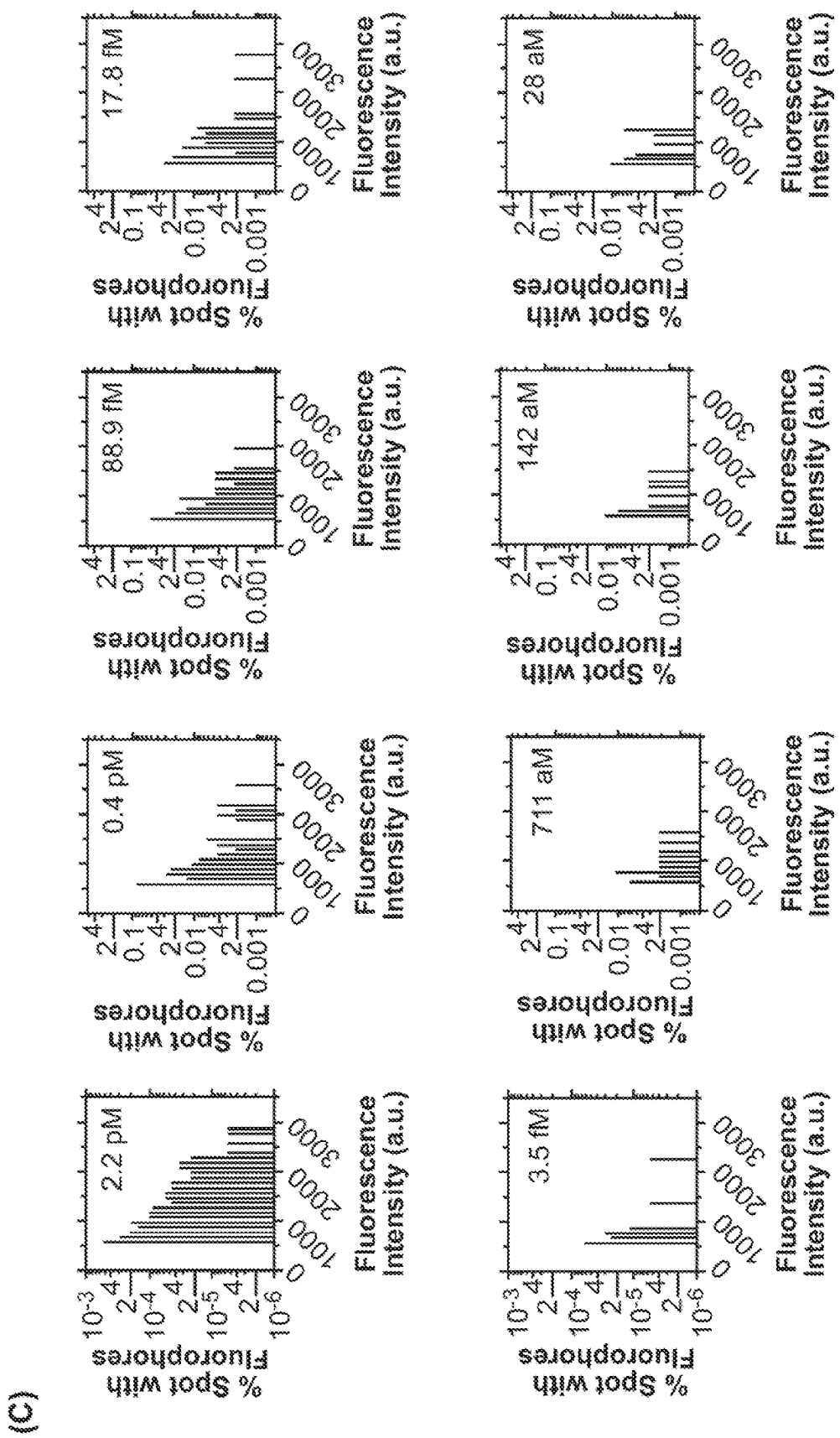
Figure 8:
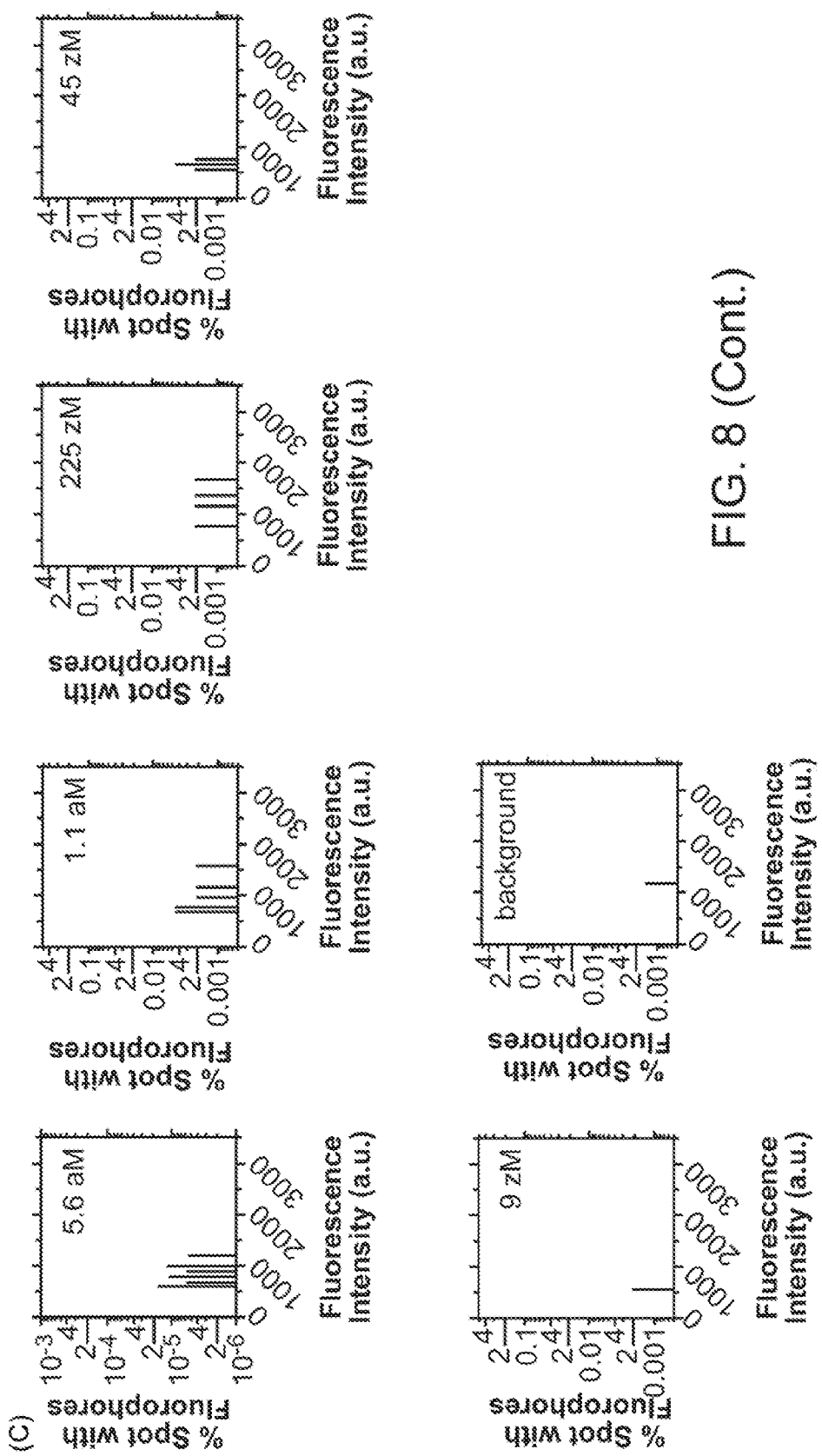

The CEA immunoassay (FIG. 7) is an indirect sandwich fluorescence immunoassay modified from a commercial immunoassay kit (R&D systems, USA). Capture antibodies (mouse anti-human CEA) were first immobilized by immersing the D2PA immunoassay plate in 100 uL of capture antibody solution with concentration of 180 ug/mL and incubate for 2 hours at room temperature. We then aspirate the solution and wash the plates with wash buffer, followed with blocking of each individual plate by immersing in 100 uL of blocking solution (R&D systems) and incubate at room temperature for 1 hour. After the same aspiration/wash process, the D2PA plates in each well were then immersed in 100 uL of CEA standards (R&D systems) in PBS solution at concentrations from 11 pM to 1.1 aM with a dilution factor of 2. They were then incubated at room temperature for 2 hours. After another washing, 100 uL of biotinylated detection antibody (goat anti-human CEA) at concentration of 200 ng/mL was added to each individual plate and incubated at room temperature for 1 hour. We then repeated the aspiration/wash process again and added 50 uL of diluted IRDye800CW labeled streptavidin at 50 ng/mL concentration (Rockland Immunochemicals) to each D2PA plate and incubate at room temperature for 1 hour. After the final washing, the D2PA plates were rinsed gently in deionized water and dried with argon gas. The plates were optically measured immediately after the immunoassay was developed. Results. For the modified three-layer-sandwich CEA assays on the D2PA plate, we have achieved an LoD of 28 aM (~0.8 fg/mL) in buffer with 8 order dynamic range, respectively, when using a conventional plate reader (area-averaged fluorescence intensity) (FIG. 8A). The new assay's LoDs are 170,000-fold better than an identical assay performed on a standard glass plate; 20-fold more sensitive than the current best CEA immunoassays (e.g. random gold island); and 5~6 orders of magnitude more sensitive than the typical CEA level in blood plasma (4 ng/mL). See FIG. 8.

After using the conventional measuring method, we applied new method to measure the identical assay using digital counting. FIG. 8B and 8C is the surface hot spot distribution in a single field of view (FOV) of CEA immunoassays at different concentrations. One can clearly see the surface density of randomly distributed emitters is proportional to the concentration of CEA. One also notices that at high concentrations >1 pM, e.g., 11 pM and 2.2 pM.

Some hot spots are clustered therefore hard to differentiate. In these cases, we integrate the overall fluorescence hot spot clusters intensity instead of counting digitally. See FIG. 8

Application

The applications of the subject sensor include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

What is claimed is:

1. A method of sample analysis, comprising:
   (a) binding target analytes to capture agents that are attached to a surface of a plate, wherein the plate comprises (i) a sensing amplification layer comprising nanostructures that enhance signals and (ii) the capture agents, wherein the capture agents are attached to said sensing amplification layer;
   (b) reading the plate with a reading device to produce an image of signals that represent individual binding events, wherein the reading is done at a resolution sufficient to distinguish between individual binding events and the image shows bright spots that are spatially separated from one another that correspond to individual binding events between a single molecule of target analyte and a single molecule of capture agent;
   (c) identifying the bright spots in an area of the image; and
   (d) counting the bright spots identified in step (c), thereby providing an estimate of the amount of one or more analytes in the sample.

2. The method of claim 1, wherein the target analytes comprise proteins, peptides, DNA, RNA, nucleic acid, small molecules, cells, or nanoparticles with different shapes.

3. The method of claim 1, wherein the capture agent specifically binds to the target analyte.

4. The method of claim 1, wherein the image shows the position, local intensity, and local spectrum of the signals.

5. The method of claim 1, wherein the signals are luminescence signals selected from the group consisting of fluorescence, electroluminescence, chemiluminescence, and electrochemiluminescence signals.

6. The method of claim 1, wherein the signals are Raman scattering signals.

7. The method of claim 1, wherein the signals are the forces due to local electrical, local mechanical, local biological, or local optical interaction between the plate and the reading device.

8. The method of claim 1, further comprising, before step (b), labeling the target analytes with a label, either prior to or after they are bound to said capture agent.

9. The method of claim 1, wherein the reading step (b) is performed by applying a voltage bias between said signal amplification layer and another electrode, thereby providing greater sensitivity.

10. The method of claim 1, wherein the identifying and counting steps comprise (1) determining the local intensity of background signal, (2) determining local signal intensity for one label, two labels, three labels, and four or more labels; and (3) determining the total number of labels in the imaged area.

11. The method of claim 1, wherein the identifying and counting steps comprise (1) determining the local spectrum of background signal, (2) determining local signal spectrum for one label, two labels, three labels, and four or more labels; and (3) determining the total number of labels in the imaged area.

12. The method of claim 1, wherein the identifying and counting steps comprise (1) determining the local Raman signature of background signal, (2) determining local signal Raman signature for one label, two labels, three labels, and four or more labels; and (3) determining the total number of labels in the imaged area.

13. The method of claim 1, wherein the identifying and counting steps comprise determining one or more of the local intensity, spectrum, and Raman signatures.

14. The method of claim 1, wherein the binding step (a) is accelerated by applying an electric field to the plate, thereby moving the analytes to the sensing amplification layer.

15. The method of claim 1, wherein the sensing amplification layer has a molecular linking layer that links said capture agents with said sensing amplification layer.

16. The method of claim 1, wherein the signals are light signals.

17. The method claim 1, wherein the signals are produced by a fluorescent label, that is associated with the bound analyte, either before or after binding of the analyte to the capture agent.

18. The method of claim 1, wherein the average distance between the two adjacent signals being read to form the image of signals in reading step is greater than 10 nm.

19. The method of claim 1, wherein the signals are signals generated by Raman scattering.

20. The method of claim 1, wherein the capture agent is an antibody.

21. The method of claim 1, wherein the capture agent is a polynucleotide.

22. A method of sample analysis, comprising:
(a) binding target analytes to capture agents that are attached to a surface of a plate, wherein the surface of the plate comprises (i) a dots-on pillar antenna array (D2PA) comprising nanostructures that enhance signals and (ii) the capture agents, wherein the capture agents are attached to said dots-on pillar antenna array;
(b) reading the plate with a reading device to produce an image of signals that represent individual binding events, wherein the reading is done at a resolution sufficient to distinguish between individual binding events and the image shows bright spots that are spatially separated from one another that correspond to individual binding events between a single molecule of target analyte and a single molecule of capture agent;
(c) identifying the bright spots in an area of the image; and
(d) counting the bright spots identified in step (c), thereby providing an estimate of the amount of one or more analytes in the sample.

23. A method of sample analysis, comprising:
(a) binding target analytes to capture agents are attached to a surface of a plate, wherein the surface of the plate comprises (i) a sensing amplification layer comprising nanostructures that enhance signals and (ii) the capture agents, wherein the capture agents that are attached to said sensing amplification layer and The method of claim 1, wherein the sensing amplification layer comprises one or a plurality of metallic discs and a flat metallic film, wherein a portion of the metallic disc has a separation from the metallic film and the separation and the dimensions of the disks are less than the wavelength of the light used in sensing;
(b) reading the plate with a reading device to produce an image of signals that represent individual binding events, wherein the reading is done at a resolution sufficient to distinguish between individual binding events and the image shows bright spots that are spatially separated from one another that correspond to individual binding events between a single molecule of target analyte and a single molecule of capture agent;
(c) identifying the bright spots in an area of the image; and
(d) counting the bright spots identified in step (c), thereby providing an estimate of the amount of one or more analytes in the sample.

24. The method of claim 23, wherein the metallic disk has a shape selected from the group of shapes consisting of round, polygonal, pyramidal, elliptical, elongated bar shaped, and any combination thereof.

25. The method of claim 23, wherein the separation is 0.5 to 30 nm, and wherein the discs have an average lateral dimension in the range of 20 nm to 250 nm.

* * * * *

UNITED STATES PATENT AND TRADEMARK OFFICE
CERTIFICATE OF CORRECTION

PATENT NO. : 10,656,149 B2
APPLICATION NO. : 14/775638
DATED : May 19, 2020
INVENTOR(S) : Stephen Y. Chou et al.

Page 1 of 1

It is certified that error appears in the above-identified patent and that said Letters Patent is hereby corrected as shown below:

In the Claims

In Claim 23, Column 23, Line 21, "capture agents are attached" should read --capture agents that are attached--

In Claim 23, Column 23, Line 26, "said sensing amplification layer and The method of" should read --said sensing amplification layer and,--

In Claim 23, Column 24, Line 1, "claim 1, wherein the sensing" should read --wherein the sensing--

Signed and Sealed this
Second Day of March, 2021

Drew Hirshfeld
*Performing the Functions and Duties of the
Under Secretary of Commerce for Intellectual Property and
Director of the United States Patent and Trademark Office*